(12) United States Patent
Kubista et al.

(10) Patent No.: US 11,421,268 B2
(45) Date of Patent: Aug. 23, 2022

(54) METHODS AND COMPOSITIONS FOR NUCLEIC ACID DETECTION

(71) Applicant: Roche Molecular Systems, Inc., Pleasanton, CA (US)

(72) Inventors: Mikael Kubista, Moelndal (SE); Robert Sjöback, Partille (SE)

(73) Assignee: Roche Molecular Systems, Inc., Pleasanton, CA (US)

(*) Notice: Subject to any disclaimer, the term of this patent is extended or adjusted under 35 U.S.C. 154(b) by 455 days.

(21) Appl. No.: 15/504,620

(22) PCT Filed: Aug. 19, 2015

(86) PCT No.: PCT/IB2015/001851
§ 371 (c)(1),
(2) Date: Feb. 16, 2017

(87) PCT Pub. No.: WO2016/027162
PCT Pub. Date: Feb. 25, 2016

(65) Prior Publication Data
US 2017/0233801 A1    Aug. 17, 2017

Related U.S. Application Data

(60) Provisional application No. 62/039,207, filed on Aug. 19, 2014.

(51) Int. Cl.
*C12Q 1/6853* (2018.01)
*C12Q 1/6816* (2018.01)
*C12Q 1/6858* (2018.01)

(52) U.S. Cl.
CPC ......... *C12Q 1/6853* (2013.01); *C12Q 1/6816* (2013.01); *C12Q 1/6858* (2013.01)

(58) Field of Classification Search
CPC .......... C12Q 2537/1373; C12Q 1/6816; C12Q 1/6858; C12Q 1/6853; C12Q 2525/155;
(Continued)

(56) References Cited

U.S. PATENT DOCUMENTS

2011/0212846 A1   9/2011  Spier
2012/0065105 A1*  3/2012  Kuersten ............. C12Q 1/6816
                                                              506/16

FOREIGN PATENT DOCUMENTS

EP      2653559 A1    10/2013
JP      2013530698 A   8/2013
(Continued)

OTHER PUBLICATIONS

RNAfold result for Seq ID No. 70 of Park et al. (obtained from http://rna.tbi.univie.ac.at//cgi-bin/RNAWebSuite/RNAfold.cgi?PAGE=3&ID=Oyozhl05f1) (Year: 2019).*

(Continued)

*Primary Examiner* — Teresa E Strzelecka
(74) *Attorney, Agent, or Firm* — Jennifer Rosenfield

(57) ABSTRACT

Methods, compositions, reaction mixtures, kits, and/or systems for producing a complementary sequence to a region in a target polynucleotide in a sample are provided. In some aspects, the methods, compositions, reaction mixtures, kits, and/or systems comprise subjecting the sample to a nucleic acid amplification reaction in a reaction mixture under conditions to yield the complete sequence to the region of the target polynucleotide. In some aspects, the complementary sequence produced is amplified.

21 Claims, 19 Drawing Sheets

Specification includes a Sequence Listing.

(58) Field of Classification Search
CPC ........ C12Q 2525/161; C12Q 2525/185; C12Q 2525/207; C12Q 2533/101; C12Q 2535/125
See application file for complete search history.

(56) References Cited

FOREIGN PATENT DOCUMENTS

| WO | WO2006115570 A2 | 11/2007 |
| WO | WO2013166466 A1 | 11/2013 |
| WO | WO2014014988 A2 | 2/2014 |

OTHER PUBLICATIONS

Jonstrup, A.T. et al., DNA Hairpins as Temperature Switches, Thermometers and Ionic Detectors, Sensors, vol. 13, pp. 5937-5944 (Year: 2013).*

Chun J-Y et al., Dual priming oligonucleotide system for the multiplex detection of respiratory viruses and SNP genotyping of CYP2C19 gene, Nucleic Acids Research, online Feb. 7, 2007, p. e40 (1-6), vol. 35, No. 6.

International Search Report dated Apr. 13, 2016 in Application No. PCT/IB2015/001851, 5 pages.

* cited by examiner

|  | Synthetic miRNA target | | |
|---|---|---|---|
|  | let-7a | let-7c | let-7x |
| Cq value | 20.985 | 23.18 | 27.06 |
| Relative detection (%) | 100 | 21.8 | 1.48 |

| Target | Let 7 sequence | RT loop primer | Forward qPCR primer | Reverse qPCR primer |
|---|---|---|---|---|
| let-7a | UGAGGUAGUAGGUUGUAUAGUU | TACTACCTCACCCCACCACGTACGGCTAGAAGACGTACCATCTGCAAACTA | TACTACCTCACCCACCACG | GCGGCTGAGGTAGTAGGTTGTATA |
| let-7b | UGAGGUAGUAGGUUGUGUGGUU | TACTACCTCACCCCACCACGTACGGCTAGAAGACGTACCATCTGCAAACCAC | TACTACCTCACCCCACCACG | CGGCTGAGGTAGTAGGTTGTG |
| let-7b | UGAGGUAGUAGGUUGUGUGUU | TACTACCTCACCCCACCACGTACGGCTAGAAGACGTACCATCTGCAAACC | TACTACCTCACCCACCACG | CGGCTGAGGTAGTAGGTTGTG |
| let-7c | UGAGGUAGUAGGUUGUAUGGUU | TACTACCTCACCCCACCACGTACGGCTAGAAGACGTACCATCTGCAAACCA | TACTACCTCACCCACCACG | GCGGCTGAGGTAGTAGGTTGTA |
| let-7c | UGAGGUAGUAGGUUGUAUGGUU | TACTACCTCACCCCACCACGTACGGCTAGAAGACGTACCATCTGCAAACCAT | TACTACCTCACCCACCACG | CGGCTGAGGTAGTAGGTTGTATG |
| let-7d | AGAGGUAGUAGGUUGCAUAGUUGCAAACCAT | TACTACCTCTCCACCACGTACGGCTAGAAGACGTACCATCTGCAACTATG | TACTACCTCTCCACCACG | CGGCAGAGGTAGTAGGTTGC |
| let-7e | UGAGGUAGGAGGUUGUAUAGU- | TCCTACCTCACCCACCACGTACGGCTAGAAGACGTACCATCTGCAACTATA | TCCTACCTCACCCACCAC | GCGGCTGAGGTAGGAGG |

B

| | A | B | C | D | E | RT- | NTC |
|---|---|---|---|---|---|---|---|
| RT10a | 16.20 | 22.90 | 22.10 | 26.31 | 29.44 | 37.19 | |
| RT10b.1 | 28.70 | 11.31 | 14.36 | 29.80 | 35.77 | 38.30 | 39.45 |
| RT10b.2 | 28.50 | 20.03 | 26.01 | 32.08 | 34.93 | 44.39 | |
| RT10c.1 | 21.27 | 20.23 | 13.94 | 22.84 | 31.24 | 39.38 | 44.63 |
| RT10c.2 | 16.09 | 12.41 | 10.09 | 25.91 | 31.11 | 36.35 | 39.13 |
| RT10d | 13.50 | 17.70 | 15.66 | 10.24 | 25.89 | 32.19 | 37.46 |
| RT10e | 27.19 | 29.74 | 28.07 | 29.78 | 17.19 | 30.96 | 30.37 |

C

| | A | B | C | D | E |
|---|---|---|---|---|---|
| RT10a | 100.0% | 1.0% | 1.7% | 0.1% | 0.0% |
| RT10b.1 | 0.0% | 100.0% | 12.1% | 0.0% | 0.0% |
| RT10b.2 | 0.3% | 100.0% | 1.6% | 0.0% | 0.0% |
| RT10c.1 | 0.6% | 1.3% | 100.0% | 0.2% | 0.0% |
| RT10c.2 | 1.6% | 20.1% | 100.0% | 0.0% | 0.0% |
| RT10d | 10.4% | 0.6% | 2.3% | 100.0% | 0.0% |
| RT10e | 0.1% | 0.0% | 0.1% | 0.0% | 100.0% |

FIG. 10

| Reaction ID | Loop primer sequence | Target | Average Cq |
|---|---|---|---|
| RT10 | TACTACCTCACCCACCACGTACGGCTAGAAGACGTACCATCTGCAAACTA | Let7a | 16.12 |
| | | Neg Ctrl | 34.86 |
| RT18 | TACTACCTCAACTCCCTCGCGTTCGTTGTTCGACCGCACTCCGTCAACTA | Let7a | 16.07 |
| | | Neg Ctrl | |
| RT19 | TACTACCTCAACTCCTTCCCGTTCGTTGTTCGACCGGACTCCGTTAACTA | Let7a | 16.44 |
| | | Neg Ctrl | 37.57 |
| RT20 | TACTACCTCAACTCCTTCTCGGTTCGTTGTTCGACCCGACTCCGTTAACTA | Let7a | 16.29 |
| | | Neg Ctrl | 39.41 |

FIG. 12

| tested parameter | group | RT | characteristic | qPCR primer for testing |
|---|---|---|---|---|
| length of 3' complementary sequence | C | RT11 | 10-8-61.1(19)-14-5 | 7a_fw7.3 + 7a_rv9 |
| | | RT12 | 10-8-61.1(19)-14-4 | 7a_fw7.3 + 7a_rv9 |
| | | RT13 | 10-8-61.1(19)-14-3 | 7a_fw7.3 + 7a_rv9 |

| Sample | Content | RT11 | SD | Tm | RT12 | SD | Tm | RT13 | SD | Tm |
|---|---|---|---|---|---|---|---|---|---|---|
| 55.0 | cDNA | 20,38 | 0,08 | 78,50 | 28,28 | 0,26 | 78,50 | 22,24 | 0,08 | 79,00 |
| | RT- | 29,81 | 0,88 | 78,00 | 33,08 | 0,07 | 78,00 | 31,07 | 1,40 | 77,75 |
| 49.2 | cDNA | 21,51 | 0,65 | 78,75 | 28,95 | 0,35 | 78,75 | 24,66 | 0,53 | 79,25 |
| | RT- | 29,31 | 0,22 | 78,00 | 33,90 | 0,18 | 78,00 | 31,99 | 2,07 | 77,75 |
| 41.5 | cDNA | 22,36 | 0,36 | 78,50 | 29,01 | 0,14 | 78,75 | 24,97 | 0,22 | 79,25 |
| | RT- | 29,89 | 0,22 | 78,00 | 32,91 | 0,15 | 78,00 | 31,28 | 0,52 | 78,00 |
| 37.0 | cDNA | 18,69 | 0,42 | 78,75 | 26,34 | 0,14 | 79,00 | 23,38 | 0,17 | 79,25 |
| | RT- | 30,48 | 0,40 | 78,00 | 34,13 | 0,56 | 77,50 | 32,21 | 0,12 | 78,00 |
| 31.0 | cDNA | 18,78 | 0,40 | 78,50 | 23,89 | 0,23 | 79,00 | 22,42 | 0,14 | 79,25 |
| | RT- | 30,22 | 0,61 | 78,00 | 33,38 | 0,19 | 77,75 | 31,32 | 0,15 | 78,00 |
| | NTC | 36,90 | 0,59 | | 36,90 | 0,59 | | 36,90 | 0,59 | |

FIG. 13

| RT | sequence (5'-3') | bp | %GC | hairpin |
|---|---|---|---|---|
| RT10 | TACTACCTCACCCACCACGTACGGCTAGAAGACGTACCATCTGCAAACTA | 50 | 50.0 | ok |
| RT10.1 | CTACCTCACCCACCACGTACGGCTAGAAGACGTACCATCTGCAAACTA | 48 | 52.1 | ok |
| RT10.2 | CCTCACCCACCACGTACGGCTAGAAGACGTACCATCTGCAAACTA | 45 | 53.3 | ok |
| RT10.3 | CTCACCCACCACGTACGGCTAGAAGACGTACCATCTGCAAACTA | 44 | 52.3 | ok |
| RT10.4 | TCACCCACCACGTACGGCTAGAAGACGTACCATCTGCAAACTA | 43 | 51.2 | ok |
| RT10.5 | TACTACCTCACCCACCACGTACGGCTAGAAGACGTACCATCTGCAAACTAT | 51 | 49.0 | ok |
| RT10.6 | TACTACCTCACCCACCACGTACGGCTAGAAGACGTACCATCTGCAAACTATA | 52 | 48.1 | ok |

| Sample | Content | AV | SD | Tm |
|---|---|---|---|---|
| RT10.0 | Unkn | 16,92 | 0,03 | 77,00 |
|  | Neg Ctrl | 32,22 | 0,50 | 76,50 |
| RT10.1 | Unkn | 18,89 | 0,43 | 77,00 |
|  | Neg Ctrl | 30,48 | 0,59 | 76,50 |
| RT10.2 | Unkn | 25,41 | 0,19 | 76,50 |
|  | Neg Ctrl | 30,60 | 0,40 | 76,50 |
| RT10.3 | Unkn | 26,68 | 0,26 | 76,50 |
|  | Neg Ctrl | 31,85 | 0,35 | 75,75 |
| RT10.4 | Unkn | 27,19 | 0,90 | 76,50 |
|  | Neg Ctrl | 33,12 | 0,71 | 76,50 |
| RT10.5 | Unkn | 14,14 | 0,02 | 77,00 |
|  | Neg Ctrl | 32,37 | 0,46 | 76,75 |
| RT10.6 | Unkn | 14,26 | 0,00 | 77,00 |
|  | Neg Ctrl | 31,49 | 0,13 | 76,50 |

FIG. 14

| testing parameter | variant | sequence (5'-3') | length (bp) | GC in 5' arm (%) |
|---|---|---|---|---|
| arm length | X | CAACCTGCCAACCGGAC~ ~TCTGCTCAACTA | 12+7 | 66.7 |
| | Y | CAACCTGCGAGACTCTACAT~ ~GTACTGCTCAACTA | 15+10 | 46.7 |
| | Z | CAACCTGCGAGACTCTACATGA~ ~GTACTGCTCAATGAAACTA | 17+14 | 47.1 |

| Sample | Content | RT5 | SD | Tm | RT2 | SD | Tm | RT6 | SD | Tm |
|---|---|---|---|---|---|---|---|---|---|---|
| 55.0 | cDNA | 24.23 | 0.45 | 78.00 | 22.99 | 0.10 | 78.50 | 24.38 | 0.42 | 76.50 |
| | RT- | 34.35 | 0.20 | 78.50 | 36.37 | 0.96 | 70.50 | 34.87 | #DIV/0! | #DIV/0! |
| 49.2 | cDNA | 23.83 | 1.08 | 78.00 | 22.95 | 1.92 | 76.75 | 25.58 | 1.94 | 78.50 |
| | RT- | 32.94 | 0.31 | 78.50 | 34.40 | 1.34 | 70.00 | 35.73 | 1.88 | 69.50 |
| 41.5 | cDNA | 24.18 | 0.07 | 78.00 | 23.01 | 0.18 | 78.50 | 26.12 | 0.04 | 78.50 |
| | RT- | 32.78 | 0.69 | 78.50 | 35.26 | 0.10 | 70.00 | 37.33 | 0.76 | #DIV/0! |
| 37.0 | cDNA | 24.14 | 0.04 | 78.00 | 21.77 | 0.39 | 78.50 | 26.46 | 2.03 | 76.75 |
| | RT- | 34.79 | 2.12 | 78.50 | 35.72 | 0.77 | 70.00 | 38.97 | 0.42 | 70.00 |
| 31.0 | cDNA | 24.89 | 0.13 | 78.00 | 21.91 | 0.37 | 77.00 | 24.74 | 0.14 | 76.75 |
| | RT- | 35.14 | 0.47 | 78.50 | 37.48 | 0.40 | 70.50 | 38.37 | #DIV/0! | 70.25 |
| | NTC | | | | 39.55 | | 69.80 | 39.43 | | |

FIG. 15

| RT | fw | rv |
|---|---|---|
| RT10.m1 | 7a_fw7.2.m1 | 7a_rv7 |
| RT10b.1 | 7a_fw7.2 | 7b_rv1 |
| RT10b.2 | 7a_fw7.2 | 7b_rv1 |
| RT10c.1 | 7a_fw7.2 | 7a_rv9 |
| RT10c.2 | 7a_fw7.2 | 7c_rv2 |
| RT10d.1 | 7d_fw1 | 7d_rv1 |
| RT10e.1 | 7e_fw1 | 7e_rv1 |

| Target | Sample | Cq AV | Cq SD |
|---|---|---|---|
| cDNA | 3000 | 11.37 | 0.19 |
| | 2000 | 11.29 | 0.14 |
| | 1500 | 11.27 | 0.11 |
| | 1000 | 10.98 | 0.31 |
| | 0 | 10.84 | 0.40 |
| RT- | 3000 | 40.29 | 0.58 |
| | 2000 | 36.05 | 0.39 |
| | 1500 | 34.25 | 0.49 |
| | 1000 | 30.17 | 0.13 |
| | 0 | #DIV/0! | #DIV/0! |
| NTC | 3000 | 40.54 | 0.03 |
| | 2000 | 37.14 | 1.09 |
| | 1500 | 38.00 | 0.07 |
| | 1000 | 34.82 | 0.20 |
| | 0 | 36.29 | 0.76 |

| Target | Oligo conc (nM) | Cq AV | Cq SD |
|---|---|---|---|
| RT 10d.1 | 1000 | 34.25 | 0.39 |
| | 500 | 31.83 | 0.23 |
| | 100 | 29.88 | 0.15 |
| | 50 | 29.60 | 0.14 |
| | 10 | 29.34 | 0.18 |
| | 1 | 29.26 | 0.06 |
| | 0.1 | 29.22 | 0.06 |
| | 0.01 | 29.33 | 0.10 |
| | 0 | 29.03 | 0.07 |

| Target | Sample | Cq AV | Cq SD |
|---|---|---|---|
| RT 10d.1 | 4000 | 44.93 | 1.14 |
| | 3000 | | 0.13 |
| | 2000 | 43.94 | 1.05 |
| | 1500 | 40.87 | 0.11 |
| | 1000 | 35.15 | 0.05 |
| | 500 | 31.64 | 0.06 |
| | 100 | 29.58 | 0.13 |
| | 50 | 29.19 | 0.60 |
| | 0 | 28.74 | |
| NTC | | 36.05 | |

FIG. 16B

|  |  | RT2 |  | RT10 |  | RT11 |  |
|---|---|---|---|---|---|---|---|
| Sample | Content | RT AV | RT SD | RT AV | RT SD | RT AV | RT SD |
| 500 | cDNA | 23,69 | 0,04 | 15,80 | 0,16 | 16,21 | 0,09 |
|  | RT- | 31,04 |  | 30,79 |  | 33,78 |  |
| 250 | cDNA | 22,36 | 0,38 | 15,04 | 0,18 | 15,42 | 0,11 |
|  | RT- | 35,34 |  | 30,84 |  | 33,67 |  |
| 100 | cDNA | 21,77 | 0,60 | 14,50 | 0,02 | 15,06 | 0,12 |
|  | RT- | 34,48 |  | 31,32 |  | 33,99 |  |
| 50 | cDNA | 21,72 | 0,29 | 14,62 | 0,08 | 14,99 | 0,22 |
|  | RT- | 37,99 |  | 32,23 |  | 35,41 |  |
| 10 | cDNA | 23,35 | 0,00 | 15,53 | 0,09 | 15,18 | 0,11 |
|  | RT- | 37,12 |  | 38,49 |  | 36,40 |  |

|  | RT10 |  | RT10/ 16 |  |  |  |
|---|---|---|---|---|---|---|
| 31°C | 15,00 | 0,05 | 15,28 | 0,10 | CFX96 | 1.run |
| 28°C | 14,43 | 0,12 | 14,80 | 0,18 | CFX96 | 2.run |
| 25°C | 14,04 | 0,07 | 14,27 | 0,08 | T100 | 1.run |
| 20°C | 13,59 | 0,20 | 14,00 | 0,12 | T100 | 2.run |

FIG. 17A

|  | Replicate | AV | SD | AV | SD |
|---|---|---|---|---|---|
| RT10st | 1 | 14,10 | 0,06 | 14,09 | 0,15 |
|  | 2 | 13,96 | 0,21 |  |  |
|  | 3 | 14,00 | 0,15 |  |  |
|  | 4 | 14,29 | 0,17 |  |  |
| RTpage | 1 | 13,91 | 0,15 | 13,95 | 0,15 |
|  | 2 | 14,12 | 0,41 |  |  |
|  | 3 | 13,76 | 0,26 |  |  |
|  | 4 | 14,02 | 0,10 |  |  |
|  | RT10st vs. RT10page |  |  | P-value= | 0,26 |

|  | Length of incubation in RT at 25°C (min) | | | | |
|---|---|---|---|---|---|
| replicate | 15 | 30 | 45 | 60 | 75 |
| 1 | 15,18 | 14,93 | 14,88 | 14,40 | 14,64 |
| 2 | 14,77 | 14,67 | 14,30 | 14,29 | 14,36 |
| 3 | 14,79 | 14,52 | 14,30 | 14,60 | 14,34 |
| AV | 14,91 | 14,71 | 14,49 | 14,43 | 14,45 |
| SD | 0,23 | 0,21 | 0,34 | 0,16 | 0,17 |

FIG. 17B

METHODS AND COMPOSITIONS FOR NUCLEIC ACID DETECTION

CROSS-REFERENCE

The present application is the US National Phase Filing of PCT/IB2015/001851, filed Aug. 19, 2015, which claims priority to U.S. Provisional No. 62/039,207, filed Aug. 19, 2014, the disclosures of which are incorporated herein by reference in their entireties.

The instant application contains a Sequence Listing which has been submitted electronically in ASCII format and is hereby incorporated by reference in its entirety. Said ASCII copy, created on Feb. 14, 2017, is named 33519_SL.txt and is 11,293 bytes in size.

BACKGROUND OF THE INVENTION

Small non-coding RNAs function as important gene expression regulators in many organisms. He et al., Nat Rev Genetics 2004, 5(7): 522-31. For example, several hundred microRNAs (miRNAs) have been identified in plants and animals, including humans, mice, Drosophila, and C. elegans (Bino et al., 2004, PLoS Biol. 2(11): e363). Specifically, single-stranded miRNAs have been shown to be associated with various human diseases, such as defects in biological processes such as apoptosis, proliferation, epithelial cell morphogenesis, neural and muscle cell differentiation, fat/cholesterol/glucose homeostasis, and viral infection. See, e.g., Esquela-Kerscher A & Slack F J, Nat. Rev. Cancer, 2006, 6(4): 259-69; Michael et al., Mol. Cancer Res., 2003, 1(12): 882-91; Dimmeler S & Nicotera P, EMBO Mol. Med. 2013, 5(2): 180-90. Recent findings suggest that many miRNAs impacting these processes are abundant and stable in the circulatory system, which makes miRNAs and other similar regulatory small non-coding RNAs invaluable biomarkers for disease diagnosis and identification, as well as potential targets for therapeutics. Brase J C et al., Mol. Cancer 2010, 26(9): 306; Chen et al., Cell Res. 2008, 18(10): 997-1006.

However, small RNAs—including microRNAs—are challenging to detect and quantitate for many reasons. First, small RNAs are short; for example, microRNAs are typically about 20 nucleotides long, which is roughly the length of a conventional PCR primer. This makes PCR amplification—which is an important method for detection and quantitation—very difficult. Second, many small RNAs are closely related; for example, many members of the same miRNA family are well conserved and differ sometimes by only one nucleotide. This makes accurately analyzing the impact of a particular small RNA difficult.

Several conventional techniques have been devised to address this need, and all of them suffer from a number of profound drawbacks. For example, the first approach is stem-loop-based RT-PCR. Chen et al., Nucleic Acids Res. 2005, 33(20): e179. In this approach, an RT primer in the shape of a stem-loop binds to the last six nucleotides of a miRNA and generates an elongated cDNA. This elongated cDNA is then amplified by a miRNA-specific forward primer and a universal reverse primer. During RT-PCR, the accuracy of quantitation is supposedly ensured by a TaqMan probe. However, the drawback for using this method is that there is lack of specificity, since the user cannot utilize a melting curve analysis to control the specificity. Moreover, the TaqMan probe binds to the sequence contributed by the RT primer, which is not necessarily unique to the miRNA.

The second approach utilizes a poly-A tail to the miRNA and use tagged poly-T primers for RT. Shi et al., Biotechniques 2005, 39(4): 519-25. However, the drawbacks for using this approach are manifold. First, small RNAs with common 3' ends may be mistakenly polyadenylated. Second, the efficiency of the polyadenylation is unknown. Third, 2'-oxymethyl modifications at the small RNAs' ends block this polyadenylation. For example, plant miRNAs carry this 2-oxymethyl modification. Thus, there exists a considerable need for an alternative system that may address one or more of these drawbacks.

SUMMARY OF THE INVENTION

An advantageous system and/or method capable of specifically, accurately, and/or cheaply detecting and/or quantitating small non-coding RNAs would overcome one or more of the aforementioned technical hurdles. Such systems and/or methods would greatly facilitate harnessing the full potential of small non-coding RNAs for diagnostic or other clinical applications.

Accordingly, the present invention provides methods, compositions, reaction mixtures, kits, and/or systems for producing a complementary sequence to a region in a target polynucleotide in a sample. These methods, compositions, reaction mixtures, kits, and/or systems are particularly useful for detecting short nucleic acids. In one aspect, the present invention provides a method for producing a complementary sequence to a region in a target polynucleotide in a sample, the method comprising subjecting the sample to a nucleic acid amplification reaction in a reaction mixture under conditions to yield the complete sequence to the region of the target polynucleotide, wherein the reaction mixture comprises: (a) a loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B of the loop primer and sequence B' on the target polynucleotide, wherein sequence A' and sequence B' are oriented 5' to 3' on the target polynucleotide; and (b) a polymerase that extends sequence B of the loop primer from 5' to 3' along the target polynucleotide that serves as the template for template-directed primer extension to produce the complementary sequence of the target polynucleotide.

In one embodiment, the method further comprises amplifying the complementary sequence to a region in a target polynucleotide in a sample in the presence of a reverse primer and optionally a forward primer, wherein the reverse primer and the forward primer exhibit sequence complementarity to the amplified product and the loop primer, respectively. In some embodiments, the forward primer specifically hybridizes to a sequence in the linker sequence. In some embodiments, the reverse primer specifically hybridizes to a sequence that is complementary to a portion of the target polynucleotide that is 5' with respect to sequence A' or B'. In some embodiments, the method further comprises detecting a product of the nucleic acid amplification of producing a complementary sequence to a region in a target polynucleotide in a sample. In some embodiments, the step of detecting comprises detecting a signal from a probe in the reaction mixture that has sequence complementarity to the product. In some embodiments, sequence A is 2 nt to about 10 nt in length and sequence B is 2 nt to about 10 nt in length. In some embodiments, the combined length of sequences A and B is about 5 nt to about 20 nt. In some embodiments, the combined length of sequences A and B is sufficient to specifically hybridize to the target polynucleotide to effect the extension of the loop primer. In some embodiments, a linear concatenation of sequences B and A is at least 80% complementary to a linear concatenation of sequences A' and B' when optimally aligned. In some embodiments, a linear concatenation of sequences B and A is at least 90% complementary to a linear concatenation of sequences A' and B'. In some embodiments, the 3' end of sequence A' is within 1 nt to about 5 nt of sequence B'. In some embodiments, the linker sequence comprises one or more sequence elements selected from the group consisting of: one or more barcode sequences, one or more restriction enzyme recognition sequences, one or more oligonucleotide probe binding sequences or complements thereof, one or more sequencing primer annealing sequences or complements thereof, and a combination of these. In some embodiments, the linker sequence comprises a universal sequence common to multiple different loop primers.

In another aspect, the present invention provides a method for producing a complementary sequence to a region in a target polynucleotide in a sample, the method comprising subjecting the sample to a nucleic acid amplification reaction having a loop primer, a forward primer, a reverse primer, and a polymerase, under conditions to yield the complete sequence to the region of the target polynucleotide, wherein the reaction mixture comprises: (a) the loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B and sequence B' on the target polynucleotide, wherein sequence A' and sequence B' are oriented 5' to 3' on the target polynucleotide; (b) the polymerase that extends sequence B of the loop primer from 5' to 3' along the target polynucleotide that serves as the template for a template-directed primer extension to produce the complementary sequence of the target polynucleotide; (c) the reverse primer that exhibits sequence homology to a sequence in the target polynucleotide located 5' with respect to sequence A' or B'; and (d) the forward primer that specifically hybridizes to a sequence complementary to the loop primer. In one embodiment, the method further comprises detecting a product of the nucleic acid amplification. In some embodiments, the step of detecting comprises detecting a signal from a probe in the reaction mixture that has sequence complementarity to the product. In some embodiments, sequence A is 2 nt to about 10 nt in length and sequence B is 2 nt to about 10 nt in length. In some embodiments, the combined length of sequences A and B is about 5 nt to about 20 nt. In some embodiments, the combined length of sequences A and B is sufficient to specifically hybridize to the target polynucleotide to effect the extension of the loop primer. In some embodiments, a linear concatenation of sequences B and A is at least 80% complementary to a linear concatenation of sequences A' and B' when optimally aligned. In some embodiments, a linear concatenation of sequences B and A is at least 90% complementary to a linear concatenation of sequences A' and B'. In some embodiments, the 3' end of sequence A' is within 1 nt to about 5 nt of sequence B'. In some embodiments, the linker sequence comprises one or more sequence elements selected from the group consisting of: one or more barcode sequences, one or more restriction enzyme recognition sequences, one or more oligonucleotide probe binding sequences or complements thereof, one or more sequencing primer annealing sequences or complements thereof, and a combination of these. In some embodiments, the linker sequence comprises a universal sequence common to multiple different loop primers.

In some embodiments, the method comprises producing a complementary sequence to a region in a target polynucleotide in a sample in a single reaction mixture under conditions to yield the complete sequence to the region of the target polynucleotide, wherein the reaction mixture comprises: (a) the loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B and sequence B' on the target polynucleotide, wherein sequence A' and sequence B' are oriented 5' to 3' on the target polynucleotide; (b) the polymerase that extends sequence B of the loop primer from 5' to 3' along the target polynucleotide that serves as the template for a template-directed primer extension to produce the complementary sequence of the target polynucleotide; (c) the reverse primer that exhibits sequence homology to a sequence in the target polynucleotide located 5' with respect to sequence A' or B'; and, (d) the forward primer that specifically hybridizes to a sequence complementary to the loop primer.

In one aspect, the invention provides a method for detecting presence in a sample of a minority allele that is a sequence variant differing from a more abundant corresponding allele at a single base position. The different alleles may be detected in the same reaction or in different reactions, wherein each allele is detected using a loop primer specific to one of the alleles. In one embodiment, the method comprises subjecting the sample to a nucleic acid amplification reaction in a reaction mixture under conditions to amplify a region of the minority allele and the more abundant allele comprising the sequence variant using a pair of loop primers, wherein the reaction mixture comprises: (a) a first loop primer that comprises sequence A1, a linker sequence D1, and sequence B1, oriented from 5' to 3' on a single strand; wherein the first loop primer specifically hybridizes to the minority allele via (i) sequence complementarity between sequence A1 of the loop primer and sequence A1' on the minority allele, and (ii) sequence complementarity between sequence B1 of the loop primer and sequence B1' on the minority allele, wherein sequence A1' and sequence B1' are oriented 5' to 3' on the minority allele; (b) a second loop primer that comprises sequence A2, a linker sequence D2, and sequence B2, oriented from 5' to 3' on a single strand; wherein the second loop primer specifically hybridizes to the more abundant allele via (i) sequence complementarity between sequence A2 of the loop primer and sequence A2' on the more abundant allele, and (ii) sequence complementarity between sequence B2 of the loop primer and sequence B2' on the minority allele, wherein sequence A2' and sequence B2' are oriented 5' to 3' on the more abundant allele; and (c) a polymerase that extends sequence B1 and sequence B2 of the first and second loop primers from 5' to 3' along the respective allele that serves as template for template-directed primer extension to produce complementary sequence of the respective alleles. In another embodiment, the method comprises subjecting portions of the sample to nucleic acid amplification reactions in reaction mixtures under conditions to amplify a region of the minority allele and the more abundant allele comprising the sequence variant using a pair of loop primers; wherein a first reaction mixture comprises a first loop primer and a polymerase, a second reaction mixture comprises a second loop primer and a polymerase, and further wherein: (a) the first loop primer comprises sequence A1, a linker sequence D1, and sequence B1, oriented from 5' to 3' on a single strand; wherein the first loop primer specifically hybridizes to the minority allele via (i) sequence complementarity between sequence A1 of the loop primer and sequence A1' on the minority allele, and (ii) sequence complementarity between sequence B1 of the loop primer and sequence B1' on the minority allele, wherein sequence A1' and sequence B1' are oriented 5' to 3' on the minority allele; (b) the second loop primer comprises sequence A2, a linker sequence D2, and sequence B2, oriented from 5' to 3' on a single strand; wherein the second loop primer specifically hybridizes to the more abundant allele via (i) sequence complementarity between sequence A2 of the loop primer and sequence A2' on the more abundant allele, and (ii) sequence complementarity between sequence B2 of the loop primer and sequence B2' on the minority allele, wherein sequence A2' and sequence B2' are oriented 5' to 3' on the more abundant allele; and (c) a polymerase extends sequence B1 or sequence B2 of the first or second loop primer from 5' to 3' along the respective allele that serves as template for template-directed primer extension to produce complementary sequence of the respective alleles. In some embodiments, the single base position at which the two alleles differ is spanned by A1/A2 or B1/B2. In some embodiments, the two alleles differ at two positions, where one position is spanned by A1/A2 and a second position is spanned by B1/B2. The sequence of D1 can be the same as or different from the sequence of D2. Where the sequences of D1 and D2 differ, amplification products of the first and second loop primers may be amplified and or detected selectively. Amplification and detection of amplification products produced using the pair of loop primers may be performed according to any suitable method described herein.

In practicing any of the methods disclosed herein, the target polynucleotide can be a DNA molecule. In some embodiments, the target polynucleotide is an RNA molecule. In some embodiments, the target polynucleotide is a non-coding RNA molecule. In some embodiments, the non-coding RNA molecule is selected from the group consisting of: a mature microRNA molecule, a pre-microRNA molecule, a primary microRNA molecule, an siRNA molecule, a piRNA molecule, a piwiRNA, a lncRNA, an rRNA, and an shRNA molecule. In some embodiments, the target polynucleotide is less than 100 nt in length. In some embodiments, the target polynucleotide is less than 50 nt in length.

In another aspect, the present invention provides a test for single nucleate variation based on a pair of Loop primers that differ in one base position in sequences A and B, such that one recognizes one allele of the target sequence and the other recognizes a different allele of the target sequence. The loop primers differ also in the loop sequence D and can be amplified and/or detected selectively.

In another aspect, the present invention provides a composition for producing a complementary sequence to a region in a target polynucleotide in a sample, the composition comprising a loop primer, a forward primer, and a reverse primer, wherein: (a) the loop primer that comprises sequence A, a linker sequence, and sequence B, oriented from 5' to 3' on a single strand; wherein the loop primer specifically hybridizes to the target polynucleotide via (i) sequence complementarity between sequence A and sequence A' on the target polynucleotide, and (ii) sequence complementarity between sequence B and sequence B' on the target polynucleotide, wherein sequence A' and sequence B' are oriented 5' to 3' on the target polynucleotide; (b) the reverse primer that exhibits sequence homology to a sequence in the target polynucleotide located 5' with respect to sequence A'; and (c) the forward primer that specifically hybridizes to a sequence in the linker sequence. In one embodiment, the composition further comprises a detection probe that has sequence complementarity to the complementary sequence of the target polynucleotide produced by extension of the reverse primer or the forward primer. In some embodiments, sequence A is 2 nt to about 10 nt in length and sequence B is 2 nt to about 10 nt in length. In some embodiments, the combined length of sequences A and B is about 5 nt to about 20 nt. In some embodiments, the combined length of sequences A and B is sufficient to specifically hybridize to the target polynucleotide to effect the extension of the loop primer. In some embodiments, a linear concatenation of sequences B and A is at least 80% complementary to a linear concatenation of sequences A' and B' when optimally aligned. In some embodiments, a linear concatenation of sequences B and A is at least 90% complementary to a linear concatenation of sequences A' and B'. In some embodiments, the 3' end of sequence A' is within 1 nt to about 5 nt of sequence B'. In some embodiments, the target polynucleotide is a DNA molecule. In some embodiments, the target polynucleotide is an RNA molecule. In some embodiments, the target polynucleotide when utilized in the subject composition is a non-coding RNA molecule. In some embodiments, the non-coding RNA molecule is selected from the group consisting of: a mature microRNA molecule, a pre-microRNA molecule, a primary microRNA molecule, an siRNA molecule, a piRNA molecule, a piwiRNA, a lncRNA, an rRNA, and an shRNA molecule. In some embodiments, the linker sequence comprises one or more sequence elements selected from the group consisting of: one or more barcode sequences, one or more restriction enzyme recognition sequences, one or more oligonucleotide probe binding sequences or complements thereof, one or more sequencing primer annealing sequences or complements thereof, and a combination of these. In some embodiments, the linker sequence comprises a universal sequence common to multiple different loop primers.

In some embodiments, the composition for producing a complementary sequence to a region in a target polynucleotide in a sample is in a container. In some embodiments, the container is a well, a plate, a tube, a chamber, a flow cell, or a chip. In some embodiments, the composition for producing a complementary sequence to a region in a target polynucleotide in a sample is in a dehydrated form. In some embodiments, the composition for producing a complementary sequence to a region in a target polynucleotide in a sample is in the form of a kit. In some embodiments, the present disclosure provides a method of using the kit form of the composition for producing a complementary sequence to a region in a target polynucleotide in a sample comprising performing a nucleic acid amplification reaction in a reaction mixture comprising a target polynucleotide, the loop primer, the forward primer, the reverse primer, and a polymerase to yield a detectable amount of an amplicon, wherein the target polynucleotide is less than about 100 nt in length. In some embodiments, a method of using the kit form of the composition for producing a complementary sequence to a region in a target polynucleotide in a sample further comprises performing a nucleic acid amplification reaction in a reaction mixture comprising a target polynucleotide, the loop primer, the forward primer, the reverse primer, and a polymerase to yield a detectable amount of an amplicon, wherein the target polynucleotide is less than about 100 nt in length and the amplification reaction has a cycle threshold ($C_T$) of less than 30.

In another aspect, the present invention provides a reaction mixture for producing a complementary sequence to a region in a target polynucleotide in a sample, the reaction mixture comprising a loop primer, a forward primer, a reverse primer, and a polymerase wherein: (a) the loop primer that comprises sequence A, a linker sequence, and sequence B, oriented from 5' to 3' on a single strand; wherein the loop primer specifically hybridizes to the target polynucleotide via (i) sequence complementarity between sequence A and sequence A' on the target polynucleotide, and (ii) sequence complementarity between sequence B and sequence B' on the target polynucleotide, wherein sequence A' and sequence B' are oriented 5' to 3' on the target polynucleotide; (b) the reverse primer that exhibits sequence homology to a sequence in the target polynucleotide located 5' with respect to sequence A'; and (c) the forward primer that specifically hybridizes to a sequence in the linker sequence. In one embodiment, the reaction mixture further comprises a detection probe that has sequence complementarity to the complementary sequence of the target polynucleotide produced by extension of the reverse primer or the forward primer. In some embodiments, sequence A is 2 nt to about 10 nt in length and sequence B is 2 nt to about 10 nt in length. In some embodiments, the combined length of sequences A and B is about 5 nt to about 20 nt. In some embodiments, the combined length of sequences A and B is sufficient to specifically hybridize to the target polynucleotide to effect the extension of the loop primer. In some embodiments, a linear concatenation of sequences B and A is at least 80% complementary to a linear concatenation of sequences A' and B' when optimally aligned. In some embodiments, a linear concatenation of sequences B and A is at least 90% complementary to a linear concatenation of sequences A' and B'. In some embodiments, the 3' end of sequence A' is within 1 nt to about 5 nt of sequence B'. In some embodiments, the target polynucleotide is a DNA molecule. In some embodiments, the target polynucleotide is an RNA molecule. In some embodiments, the target polynucleotide when utilized in the subject composition is a non-coding RNA molecule. In some embodiments, the non-coding RNA molecule is selected from the group consisting of: a mature microRNA molecule, a pre-microRNA molecule, a primary microRNA molecule, an siRNA molecule, a piRNA molecule, a piwiRNA, a lncRNA, an rRNA, and an shRNA molecule. In some embodiments, the linker sequence comprises one or more sequence elements selected from the group consisting of: one or more barcode sequences, one or more restriction enzyme recognition sequences, one or more oligonucleotide probe binding sequences or complements thereof, one or more sequencing primer annealing sequences or complements thereof, and a combination of these. In some embodiments, the linker sequence comprises a universal sequence common to multiple different loop primers.

In some embodiments, the reaction mixture for producing a complementary sequence to a region in a target polynucleotide in a sample is in a container. In some embodiments, the container is a well, a plate, a tube, a chamber, a flow cell, or a chip. In some embodiments, the reaction mixture for producing a complementary sequence to a region in a target polynucleotide in a sample is in a dehydrated form. In some embodiments, the reaction mixture for producing a complementary sequence to a region in a target polynucleotide in a sample is in the form of a kit.

In some embodiments, a method of using the subject kit comprises performing a nucleic acid amplification reaction in a reaction mixture comprising a target polynucleotide, the loop primer, the forward primer, the reverse primer, and a polymerase to yield a detectable amount of an amplicon, wherein the target polynucleotide is less than about 100 nt in length. In some embodiments, the target polynucleotide is less than about 100 nt in length and the amplification reaction has a cycle threshold ($C_T$) of less than 30.

In another aspect, the present invention provides a system for detecting a target polynucleotide in a sample, the system comprising: (a) a computer configured to receive a customer request to perform a detection reaction on a sample; (b) an amplification system that performs a nucleic acid amplification reaction in a reaction mixture disclosed herein to produce an amplified product; and, (c) a report generator that sends a report to a recipient, wherein the report contains results for detection of a detection signal corresponding to amount of the amplified product. In one embodiment, the recipient is the customer. In some embodiments, a computer-readable medium comprises codes that, upon execution by one or more processors, implement a method of detecting a target polynucleotide in a sample, the method comprising: (a) receiving a customer request to perform a detection reaction on a sample; (b) performing a nucleic acid amplification reaction in a reaction mixture disclosed herein to produce an amplified product; and, (c) generating a report containing results for detection of a detection signal corresponding to amount of the amplified product.

In any of the various aspects of the disclosure, a linker sequence of a loop primer may comprise a hairpin structure.

The methods, compositions, reaction mixtures, kits, and/or systems of the present invention are useful for producing a complementary sequence to a region in a target polynucleotide in a sample. Reagents sufficient to accomplish both the first primer extension and subsequent amplification can be added at the same time, or at separate times. In other embodiments, the products of the first primer extension reaction can be transferred, in whole or in part, diluted or undiluted, to a separate container in which to conduct the amplification process. Non-limiting examples of suitable container include microcentrifuge tubes, conical tubes, thin-walled tubes, strip tubes, multi-well plates, microfluidic devices, and microarrays. In some embodiments, the complementary sequence to a region in a target polynucleotide in a sample or their amplification product is useful for the detection and/or quantification of the target polynucleotide in a starting material. The subject methods and devices are particularly useful for detecting genetic associations, diagnosis, prognosis and/or theranosis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A, 5B, and 50 show an exemplary analysis of RT yield generated by a specific primer according to an embodiment of the present disclosure.

FIG. 7 shows an example of discrimination between miRNAs with single nucleotide differences according to an embodiment of the present disclosure.

FIGS. 10A, 10B, and 10C show example primers and results for specific amplification of miRNA family members according to an embodiment of the present disclosure. FIG. 10A shows SEQ ID NOs:1, 17-21, 18, 22, 20, 23, 18, 22, 2, 24, 18, 16, 2, 25, 18, and 26-34 in order of appearance left to right, then top to bottom.

FIG. 12 provides an example of primers and amplification results illustrating background signal reduction according to an embodiment of the present disclosure. SEQ ID NOS 17, 12, 35 and 36 appear in order of appearance.

FIG. 13 depicts results of an exemplary analysis of the length of the 3' complementary sequence of a specific primer according to an embodiment of the disclosure.

FIG. 14 depicts results of an exemplary analysis of the length of 5' and 3' complementary sequences according to an embodiment of the disclosure. SEQ ID NOS 17 and 37-42 appear ifs order of appearance.

FIG. 15 depicts results of an exemplary analysis of the length of 5' and 3' arm sequence according to an embodiment of the disclosure. SEQ ID NOS 43-48 appear in order of appearance.

FIGS. 16A and 16B show an exemplary scheme for and results of an exemplary analysis of background reduction using a blocking oligonucleotide.

FIGS. 17A and 17B show results of an example optimization of RT-PCR conditions according to an embodiment of the disclosure. RT primer concentration was about 50 nM.

Figure 1:
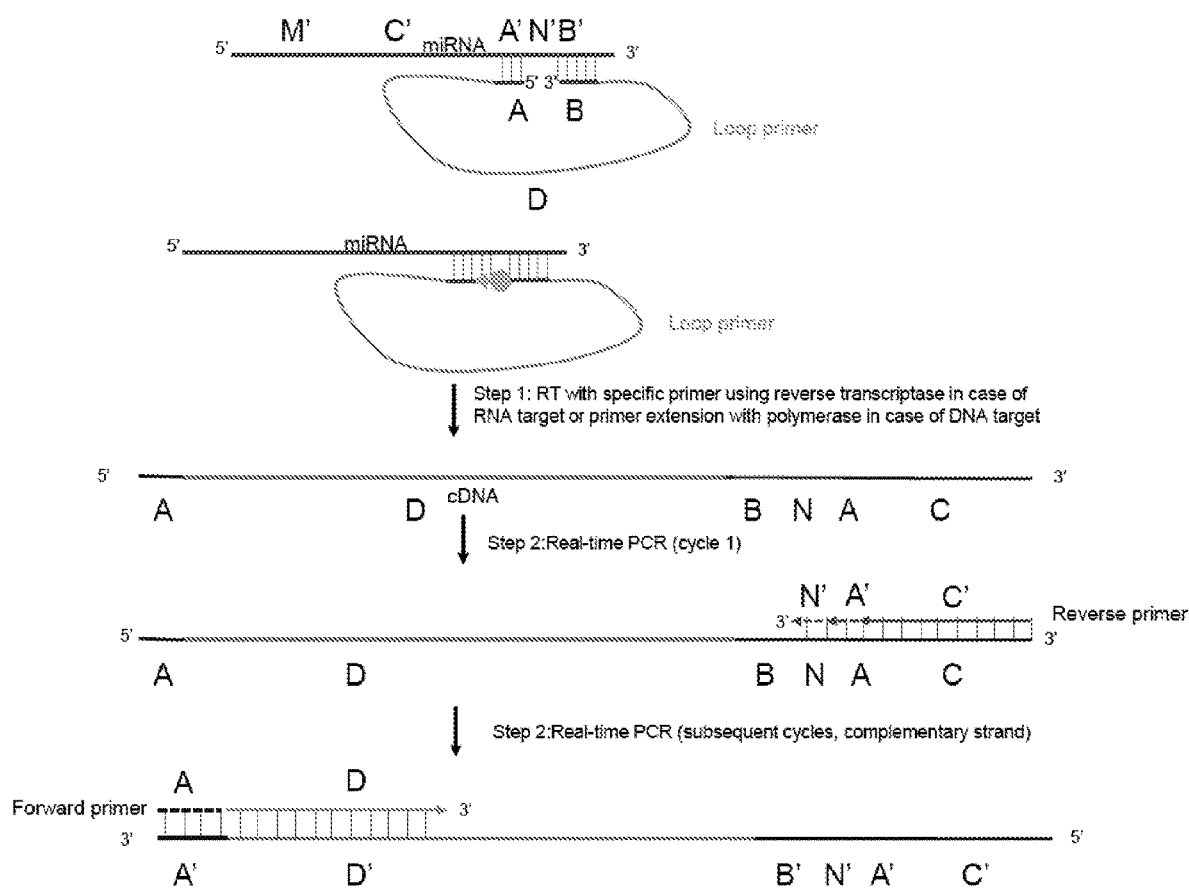
FIG. 1 shows an exemplary schematic representation of a complementary sequence amplification scheme of the present disclosure.

The temperature profile was as follows: 25° C. for 45 minutes; 85° C. for 5 minutes.

DEFINITIONS

The terms "polynucleotide," "nucleic acid," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

As used herein, the terms "target polynucleotide" and "target sequence" are used interchangeably, and refer to nucleic acid molecules or polynucleotides in a population of nucleic acid molecules having a target sequence to which one or more oligonucleotides of the invention are designed to hybridize. In some embodiments, a target sequence uniquely identifies a sequence derived from a sample, such as a particular genomic, mitochondrial, bacterial, viral, or RNA (e.g. mRNA, miRNA, primary miRNA, or pre-miRNA) sequence. In some embodiments, a target sequence is a common sequence shared by multiple different target polynucleotides, such as a common adapter sequence joined to different target polynucleotides. "Target polynucleotide" may be used to refer to a double-stranded nucleic acid molecule comprising a target sequence on one or both strands, or a single-stranded nucleic acid molecule comprising a target sequence, and may be derived from any source of or process for isolating or generating nucleic acid molecules. A target polynucleotide may comprise one or more (e.g. 1, 2, 3, 4, 5, 6, 7, 8, 9, 10, or more) target sequences, which may be the same or different. In general, different target polynucleotides comprise different sequences, such as one or more different nucleotides or one or more different target sequences.

"Hybridizes" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

"Complement," "complements," "complementary," and "complementarity" refer to a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "hybridized" as applied to a polynucleotide refers to a polynucleotide in a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, ligation reaction, sequencing reaction, or cleavage reaction.

The present invention is applicable for amplifying a variety of short RNA molecules and non-coding RNA molecules. As used herein, the term "non-coding RNA molecule" or "short RNA molecule" refers to any RNA molecule that does not encode a protein. Non-limiting examples of non-coding RNA molecules include: microRNA (miRNA), piwi-interacting RNA (piRNA), short interfering RNA (siRNA), short-hairpin RNA (shRNA), small nuclear RNA (snRNA), small nucleolar RNA (snoRNA), transfer RNA (tRNA), and ribosomal rna (rRNA). As used herein, the term "microRNA" is used to refer to any form of microRNA in the biogenesis of mature microRNA, including primary microRNA (pri-miRNA), pre-microRNA (pre-miRNA), and mature microRNA. The RNA target may be present in less than 1,000,000, 100,000, 10,000, 5,000, 2,500, 1,000, 500, or 100 copies or copies per cell.

As used herein, "mature microRNA" refers to an RNA molecule that has a length in the range of 19 to 30 nucleotides. The terms "microRNA" and "miRNA" may be used interchangeably. Non-limiting examples of miRNA known in the art include: miR-1, miR-7, miR-9*, miR-10a, miR-10b, miR-15a, miR-15b, miR-16, miR-17-3p, miR-17-5p, miR-18, miR-19a, miR-19b, miR-20, miR-21, miR-22, miR-23a, miR-23b, miR-24, miR-25, miR-26a, miR-26b, miR-27a, miR-28, miR-29a, miR-29b, miR-29c, miR-30a-5p, miR-30b, miR-30c, miR-30d, miR-30e-5p, miR-30e-3p, miR-31, miR-32, miR-33, miR-34a, miR-34b, miR-34c, miR-92, miR-93, miR-95, miR-96, miR-98, miR-99a, miR-99b, miR-100, miR-101, miR-103, miR-105, miR-106a, miR-107, miR-122, miR-122a, miR-124, miR-124, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-143, miR-144, miR-145, miR-146, miR-147, miR-148a, miR-148b, miR-149, miR-150, miR-151, miR-152, miR-153, miR-154*, miR-154, miR-155, miR-181a, miR-181b, miR-181c, miR-182*, miR-182, miR-183, miR-184, miR-185, miR-186, miR-187, miR-188, miR-189, miR-190, miR-191, miR-192, miR-193, miR-194, miR-195, miR-196a, miR-196b, miR-197, miR-198, miR-199a*, miR-199a, miR-199b, miR-200a, miR-200b, miR-200c, miR-202, miR-203, miR-204, miR-205, miR-206, miR-208, miR-210, miR-211, miR-212, miR-213, miR-213, miR-214, miR-215, miR-216, miR-217, miR-218, miR-220, miR-221, miR-222, miR-223, miR-224, miR-296, miR-299, miR-301, miR-302a*, miR-302a, miR-302b*, miR-302b, miR-302d, miR-302c*, miR-302c, miR-320, miR-323, miR-324-3p, miR-324-5p, miR-325, miR-326, miR-328, miR-330, miR-331, miR-337, miR-338, miR-339, miR-340, miR-342, miR-345, miR-346, miR-363, miR-367, miR-368, miR-370, miR-371, miR-372, miR-373*, miR-373, miR-374, miR-375, miR-376b, miR-378, miR-379, miR-380-5p, miR-380-3p, miR-381, miR-382, miR-383, miR-410, miR-412, miR-422a, miR-422b, miR-423, miR-424, miR-425, miR-429, miR-431, miR-448, miR-449, miR-450, miR-451, let7a, let7b, let7c, let7d, let7e, let7f, let7g, let7i, miR-376a, and miR-377. Further examples of targets to which the methods of the present invention apply, as well as the sequences of the above-mentioned microRNA targets, can be found in "the miRBase sequence database" as described in Griffith-Jones et al. (2004), Nucleic Acids Research 32:D109-D111, and Griffith-Jones et al. (2006), Nucleic Acids Research 34: D140-D144.

As used herein, the terms "pre-microRNA" and "pre-miRNA" are used interchangeably to refer to any molecule, the processing of which releases a mature miRNA. Pre-miRNA molecules comprise a region of secondary structure, comprising a region of double-stranded RNA and loop region formed by the sequence between the regions contributing to the double-stranded region, resulting in a hairpin-like structure. The terms "primary RNA" and "pri-miRNA" are used interchangeably to refer to any molecule, the processing of which results in a pre-miRNA. Pri-miRNAs can be from a variety of genomic sources, including without limitation distinct transcripts, intergenic regions, untranslated regions of other transcripts, and introns (including so-called "mirtrons").

As used herein, the terms "short interfering RNA" and "siRNA" are used interchangeably to refer to any RNA molecule shorter than about 50, 40, 35, 30, 25, 20, or fewer nucleotides capable of inducing silencing of a gene target based on complementarity. Silencing is typically mediated by an Argonaute protein and is typically initiated by a short RNA molecule trigger. Silencing can be post-transcriptional or transcriptional. The siRNA molecule may be completely or partially complementary to the gene or genes whose expression in reduced, and silencing may be effected with or without cleavage of an mRNA transcript. As used herein, the terms "short-hairpin RNA" and "shRNA" are used interchangeably to refer to any single-stranded RNA molecule having two regions capable of base-pairing with one another separated by a region that does not participate in base pairing, the processing of which releases one or more siRNAs. shRNAs may be of cellular (endogenous) or artificial (exogenous) origin. Endogenous siRNA includes "piRNA," which are any of a class of Piwi-interacting RNAs.

Furthermore, as will be appreciated by those skilled in the art, some miRNA can further be characterized in terms of their capacities to affect gene regulation in a wide variety of organisms and in a wide variety of tissues. A single gene may be regulated by multiple miRNAs, and miRNA regulation may act synergistically. A single miRNA may also be capable of regulating multiple mRNAs, for example, some estimates have suggested a single human miRNA may regulate up to 100-200 genes. It has also been recently described that up to 30% of human genes are targets for miRNA regulation. miRNA can be isolated from a variety of organisms, non-limiting examples of which include mammals, amphibians, insects, nematodes, plants, and many others in the range from metazoans to viruses. miRNAs may be differentially expressed between organisms, between tissues within an organism, and temporally regulated within an organism. miRNA regulation can affect multiple processes. Non-limiting examples of the processes affected by miRNA gene regulation include: differentiation, development, aging, apoptosis, oncogenesis, metabolism, cell growth, and cell proliferation (Zhou et al. (2007), BMC Genomics 8: 396; and Lu et al. (2008), PLoS ONE 3(10): e3420). As a consequence of the many pathways affected, dysregulation of miRNAs and their targets has been implicated in many diseases, non-limiting examples of which include: cardiovascular diseases, autoimmune disorders, psoriasis, viral infection, schizophrenia, lipid metabolism disorders, obesity, asthma, Down syndrome, renal function disorders, fluid homeostasis, developmental abnormalities, polycythemia vera, atopic eczema, myotonic dystrophy, Parkinson's, diabetes, neurodegeneration, Tourette's syndrome, fragile x syndrome (Lu et al. (2008), PLoS ONE 3(10): e3420). Dysregulation of miRNA and their targets has further been implicated in a number of cancers, non-limiting examples of which include: multiple myeloma, lymphoma, Burkitt lymphoma, pediatric Burkitt lymphoma, adult Burkitt lymphoma, B cell lymphoma, solid cancer, hematopoietic malignancies, colon cancer, breast cancer, cervical cancer, ovarian cancer, mantle cell lymphoma, pituitary adenomas, leukemia, prostate cancer, stomach cancer, pancreatic cancer, thyroid cancers, lung cancer, papillary thyroid cancer, bladder cancer, germ cell tumors, brain tumor, and testicular germ cell tumors. Id. As such, miRNAs can be useful as markers in diagnosing, prognosing, and theranosing disease.

As used herein, the term "homology" refers to a nucleotide sequence which is homologous to a reference nucleotide sequence. In contrast, the terms "complementary" and "complement" refer to a nucleotide sequence capable of base-pairing with a reference nucleotide sequence, such as during the hybridization phase of a PCR reaction. Furthermore, "non-complementary" is used to refer to a sequence that lacks sufficient complementary sequence to stably base-pair with a reference sequence under a given set of conditions, such as during the hybridization phase of a PCR reaction. Degree of homology and complementarity can vary in accordance with a given application, and can be more than 5%, 10%, 20%, 30%, 40%, 50%, 60%, 70%, 80%, 90%, or more than 95%. Furthermore, the term "substantially non-complementary," as used herein, refers to a nucleotide sequence that is less than about 50%, 40%, 30%, 20%, 10%, or less than about 5% complementary to a reference sequence. It is understood that purine and pyrimidine nitrogenous bases with similar structures can be functionally equivalent in terms of Watson-Crick pairing; and the inter-substitution of like nitrogenous bases, such as by methylation, does not constitute a material substitution.

As used herein, the terms "amplify," "amplifies," "amplified," "amplification," and "amplicon" refer to any method for replicating a nucleic acid with the use of a primer-dependent polymerase and/or those processes' products. In a preferred embodiment, the amplification is effected by means of PCR using a pair of primers, comprising a first and second primer as described above. Amplified products can be subjected to subsequence analyses, including but not limited to melting curve analysis, nucleotide sequencing, single-strand conformation polymorphism assay, allele-specific oligonucleotide hybridization, Southern blot analysis, and restriction endonuclease digestion.

Amplification products may be detected by the use of a probe. As used herein, the term "probe" refers to a polynucleotide that carries a detectable member and has complementarity to a target nucleic acid, thus being able to hybridize with said target and be detected by said detectable member. In certain embodiments, a probe may include Watson-Crick bases or modified bases. Modified bases include, but are not limited to, the AEGIS bases (from Eragen Biosciences), which have been described, e.g., in U.S. Pat. Nos. 5,432,272; 5,965,364; and 6,001,983. In certain aspects, bases are joined by a natural phosphodiester bond or a different chemical linkage. Different chemical linkages include, but are not limited to, a peptide bond or an LNA linkage, which is described, e.g., in published PCT applications WO 00/56748 and WO 00/66604.

The practice of the present invention employs, unless otherwise indicated, conventional techniques of biochemistry, chemistry, molecular biology, microbiology, cell biology, genomics and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), and ANIMAL CELL CULTURE (R. I. Freshney, ed. (1987)).

DETAILED DESCRIPTION OF THE INVENTION

The present invention provides methods, compositions, reaction mixtures, kits, and/or systems for producing a complementary sequence to a region in a target polynucleotide in a sample. These methods, compositions, reaction mixtures, kits, and/or systems are particularly useful for detecting short nucleic acids.

Methods:

In one aspect, the present invention provides a method for producing a complementary sequence to a region in a target polynucleotide in a sample, the method comprising: subjecting the sample to a nucleic acid amplification reaction in a reaction mixture under conditions to yield the complete sequence to the region of the target polynucleotide, wherein the reaction mixture comprises: (a) a loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B of the loop primer and sequence B' on the target polynucleotide, wherein sequence A' and sequence B' are oriented 5' to 3' on the target polynucleotide; and (b) a polymerase that extends sequence B of the loop primer from 5' to 3' along the target polynucleotide that serves as the template for template-directed primer extension to produce the complementary sequence of the target polynucleotide.

In another aspect, the present invention provides a method for producing a complementary sequence to a region in a target polynucleotide in a sample, the method comprising: subjecting the sample to a nucleic acid amplification reaction having a loop primer, a forward primer, a reverse primer, and a polymerase, under conditions to yield the complete sequence to the region of the target polynucleotide, wherein the reaction mixture comprises: (a) the loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B and sequence B' on the target polynucleotide, wherein sequence A' and sequence B' are oriented 5' to 3' on the target polynucleotide; (b) the polymerase that extends sequence B of the loop primer from 5' to 3' along the target polynucleotide that serves as the template for a template-directed primer extension to produce the complementary sequence of the target polynucleotide; (c) the reverse primer that exhibits sequence homology to a sequence in the target polynucleotide located 5' with respect to sequence A' or B'; and (d) the forward primer that specifically hybridizes to a sequence complementary to the loop primer.

The loop primer used in any of the methods or present in any of the compositions disclosed herein refers to a polynucleotide which has two stretches of complementarity to the target polynucleotide at its two ends. Sequence A used in the method is the complementary stretch at the loop primer's 5' end, and Sequence B used in the method is the complementary stretch at the loop primer's 3' end. These two sequences, used in the method, basepair to sequences A' and B' of the target polynucleotide, where A' is positioned more 5' than B'. Sequences A' and B' are very close to each other, and is separated only by a sequence of N' on the target polynucleotide, as used in the method. Sequence A and A' can be at least 2, 3, 4, 5, 6, 7, 8, 9, or 10 nucleotides. In some embodiments, sequence A is between 5-15 nucleotides in length (e.g. 10 nucleotides in length). Sequence B and B' can be at least 5, 6, 7, 8, 9, 10, 11, 12, 13, 14, 15, 16, 17, 18, 19, or 20 nucleotides. In some embodiments, sequence B is between 4-6 nucleotides in length. Sequence N' can be 1, 2, 3, 4, or 5 nucleotides. The intervening linker sequence used in the method between Sequence A and B on the loop primer, Sequence D, may be of a sufficient length to allow structural space for the loop primer to have A and B anneal to A' and B', respectively, at the same time.

In practicing any of the disclosed methods, the loop primer is generally designed to specifically hybridize to the target polynucleotide with A-A' base-pairing and B-B' base-pairing. A polymerase then extends from the 3' end of sequence B, using the target polynucleotide as the template, to generate the complementary sequence to the target polynucleotide, with the complement to regions N', A', and then the remainder of the target polynucleotide generated via template-directed primer extension, produced in that order. During template-directed primer extension, the A-A' hybridization gets knocked off as the polymerase extends from the 3' end of Sequence B. The first complementary sequence will therefore have, from 5' to 3', the following regions: A, D, B, N, A, and remainder of target polynucleotide. This complementary sequence is longer due to the length provided by sequence D. This complementary sequence may also be in a more stable form than the target polynucleotide; for example, if the target polynucleotide is a miRNA and the polymerase is a reverse transcriptase, this complementary sequence is a longer DNA polynucleotide, which is more stable.

One consideration for the design of the loop primer used in any of the subject methods or compositions is the region of complementarity selected for A-A' and B-B'. Because template-directed primer extension occurs at the 3' end of sequence B, so that only regions 5' of B' on the target polynucleotide are amplified, it is desirable that A' and B' regions are selected to be relatively close to the 3' end of the target polynucleotide. Such a selection ensures that sufficient number of target polynucleotide sequences are 5' of the A-A' and B-B' hybridization to be included in the first complementary sequence.

The length of the loop primer, Sequence A, and Sequence B will depend on many factors known in the art, such as the desired hybridization temperature of the primer, the target nucleic acid sequence, and the complexity of the different target nucleic acid sequences to be amplified. The nucleic acid sequence of the loop primer is incorporated into the sequence of each synthesized first complementary nucleic acid molecule. In some embodiments, the first complementary nucleic acid polynucleotide located at the 3' end of the loop primer is complementary to, and thus able to hybridize with, at least a portion of the target complementary nucleic acid polynucleotide, and can be at least about 3, 4, 5, 6, 7, 8, 9, 10, 11, 12, 13, 14, 15, 16, 17, 18, 19, 20 or more nucleotides in length. In some embodiments, the first complementary nucleic acid molecule comprises one or more nucleotide mismatches with the target sequence, such as 1, 2, 3, 4, 5, 6, 7, 8, 9, 10, or more mismatches. Selection of a substantially non-complementary sequence will depend on the target to be amplified. Such a substantially non-complementary sequence may be artificial or designed, such as a sequence found in another organism, a sequence found in another species, a sequence found in another sub-species, a substantially non-complementary sequence from a different member of the same species, a sequence from the same subject selected from a region substantially non-complementarity to the target, a randomly generated sequence known to be substantially-non-complementarity to the target, or a specifically designed sequence known to be substantially non-complementary to the target.

In some embodiments, sequence A used in practicing the subject methods is 2 nt to about 10 nt in length and sequence B is 2 nt to about 10 nt in length. In some embodiments, the combined length of sequences A and B is about 5 nt to about 20 nt. In some embodiments, the combined length of sequences A and B is sufficient to specifically hybridize to the target polynucleotide to effect the extension of the loop primer. In some embodiments, a linear concatenation of sequences B and A is at least 80% complementary to a linear concatenation of sequences A' and B' when optimally aligned. In some embodiments, a linear concatenation of sequences B and A is at least 90% complementary to a linear concatenation of sequences A' and B'. In some embodiments, the 3' end of sequence A' is within 1 nt to about 5 nt of sequence B'.

Another consideration for the design of the loop primer, as used in the method, is the number of nucleotides in the sequences of A-A' and B-B' hybridizations. The total number of nucleotides may increase the specificity and stability of the loop primer and target polynucleotide complex. The specificity and stability of this complex aids in accuracy in subsequent amplification and quantitation of the target polynucleotide. Where desired, the number of nucleotides in Sequence B can be greater than the number of nucleotides in Sequence A to increase the efficiency such that the A-A' hybridization is knocked off during the elongation of the primer-extension from the 3' end of Sequence B.

In some embodiments, Sequence A and B are of equal length in nucleotide bases, comprising at least 3, 4, 5, 6, 7, 8, 9 or 10, but no more than about 50 nucleotides. In another embodiment, Sequence A is 2 nucleotides and Sequence B is 3 nucleotides. In another embodiment, Sequence A is 2 nucleotides and Sequence B is 4 nucleotides. In another embodiment, Sequence A is 3 nucleotides and Sequence B is 4 nucleotides.

A related consideration for the design of the loop primer is the combined length of sequences of A and B, which is generally sufficient to allow specific hybridization to the target polynucleotide. This hybridization should be stable enough to permit time for the subsequent elongation off the 3' end of Sequence B. In some embodiments, the combined length of A and B is about 5 to 50 nucleotides, about 5 to about 10 nucleotides, or about 5 to about 15 nucleotides.

The degree of complementarity for sequences of A and B in the loop primer is generally sufficient to specifically hybridize to the target polynucleotide. This hybridization should be stable enough to permit time for the subsequent elongation off the 3' end of Sequence B. In some embodiments, the sequences of A and B are at least 80%, 85%, 90%, 95%, 96%, 97%, 98%, 99% or 100% complementary to the linear concatenations of sequences A' and B' when the sequences are optimally aligned.

The number of nucleotides in between Sequences A and B in the loop primer generally corresponds to the length of sequence N' and N, which may affect the efficiency of the polymerase extension at the 3' end of Sequence B during the first complementary strand synthesis. The larger the distance, the easier it is for polymerases to fit into the loop primer to initiate template-directed primer extension and to knock off the A-A' hybridization. However, with larger distances, specificity of binding between the loop primer and the target polynucleotide may be reduced, as the greater N' nucleotides are not specifically interacting with sequences dictated by the loop primer's Sequence A and B. In some embodiments, the 3' end of sequence A' is within 1 nt to about 10 nt, within 1 nt to about 5 nt, or within 2 nt to about 5 nt, of the 5' end of sequence B'.

Loop primers can be designed to detect single nucleotide variation. For example, the subject method may utilize a pair of loop primers that differ in one base position in sequences A and B, such that one recognizes one allele of the target sequence and the other recognizes a different allele of the target sequence. The loop primers differ also in the loop sequence D and can be amplified and/or detected selectively.

In one embodiment, one loop primer binds the allelic nucleotide as well as adjacent sequences and another loop primer binds immediately adjacent sequences to the allelic nucleotide; the former captures just one allele, while the latter captures both alleles. During subsequent detection, quantitation, and amplification steps, the two loop primers, which may have different linker sequences, can be differentiated selectively, which in turns allows the different alleles of the target polynucleotide to be differentially detected, quantitated, and amplified from the first complementary sequence.

The linker sequence D in a subject loop primer is generally designed to have a sufficient length for hybridization of both A-A' and B-B', which in turn increases the specificity of the loop primer in binding to the correct small RNA target. In one embodiment, the linker sequence is from about 5 to about 100, 10 to about 80, or 20 to about 50 nucleotides. In some other embodiments, the linker sequence is about 10, 20, 30, 40, 50, 60, 70, 80, 90 or about 100 nucleotides in length.

Where desired, the linker sequence used in the subject methods or present in the subject compositions can comprise one or more sequence elements, including but not limited to one or more barcode sequences, one or more restriction enzyme recognition sequences, one or more oligonucleotide probe binding sequences or complements thereof, one or more sequencing primer annealing sequences or complements thereof, one or more common sequences shared among multiple different loop primers or subsets of different loop primers, one or more pairs of complementary sequences for the formation of a hairpin structure, or a combination of these. In some embodiments, the linker sequence comprises a universal sequence common to multiple different loop primers. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. A sequence element may be of any suitable length, such as about, less than about, or more than about 3, 4, 5, 6, 7, 8, 9, 10, 15, 20, 25, 30, 35, 40, 45, 50 or more nucleotides in length.

In some embodiments, the linker sequence comprises one or more pairs of complementary sequences for the formation of a hairpin structure. Each sequence in a pair of sequences may be referred to as a "stem sequence." Stem sequences in a pair of stem sequences may be perfectly complementary over their entire length, or may comprise one or more (e.g. 1, 2, 3, 4, 5, or more) mismatches. In some embodiments, stem sequences in a pair of stem sequences are at least 80%, 85%, 90%, 95%, or 100% complementary. A stem sequence can be of any suitable length, such as about or at least about 3, 4, 5, 6, 7, 8, 9, 10, 15, 20, 25, or more nucleotides in length. In some embodiments, stem sequences are between 5-10 nucleotides in length (e.g. 7 nucleotides in length). Stem sequences may be designed such that the stem formed by their hybridization has a specified melting temperature (Tm), such as between 35-90° C., 40-75° C., 45-65° C., or 50-55° C. In some embodiments, the stem formed by hybridization between the stem sequences has a Tm between 60-72° C. The location of each stem sequence within the linker sequence can be varied. In general, the sequence within the linker between stem sequences forms a loop structure upon hybridization between the stem sequences. Distance between the stem sequences can affect the length of the sequence forming the loop, such as a loop sequence that is at least about 3, 4, 5, 6, 7, 8, 9, 10, 15, 20, 25, or more nucleotides in length. In some embodiments, the loop sequence is between 5-10 nucleotides in length (e.g. 5 nucleotides in length). A loop sequence may be designed to be devoid of target binding sequences (e.g. sequences complementary to a miRNA target). A stem may include a nucleotide immediately preceding a nucleotide in the loop primers sequence A and/or sequence B. Alternatively, a loop primer may comprise one or more (e.g. 1, 2, 3, 4, 5, 6, 7, 8, 9, 10, 15, 20, 25, or more) nucleotides between the end of a stem sequence and the start of one or both of sequence A or sequence B, which sequences may be referred to as "arm sequences". A loop primer that comprises a linker sequence forming a hairpin structure may comprise none, one, or two arms, with the length of each arm selected independently of the other. In some embodiments, one or both arms are designed to be between 5-15 nucleotides in length.

In some embodiments, the linker sequence comprises unique sequences to aid in the subsequent detection, quantitation of the produced complementary sequence of the target polynucleotide of interest. After producing the first complement sequence, portions of the linker sequence is complementary to the forward primer. Therefore, having specific barcodes within the linker sequence may allow different loop primers to be amplified, detected, or quantitated by different forward but the same reverse primers. In some embodiments, one loop primer's sequence A and B may bind to slightly different regions of the same target polynucleotide than another loop primer's sequence A and B, which allows greater specificity and/or user verification. Subsequent amplification, detection, and quantitation of these different loop primers can be facilitated by different forward primers binding differently due to different barcodes in the linker sequence.

In some embodiments, the linker comprises one or more restriction enzyme recognition sequences. After amplification, the accuracy of the detection can be markedly improved with a restriction digest, so that only genuine products amplified from the first complement sequence, containing the linker sequence restriction site, is cleaved and tabulated for detection and quantitation.

In other embodiments, the linker sequence comprises one or more oligonucleotide probe binding sequences, complements of oligonucleotide probe binding sequences, primer annealing sequences, or complements of primer annealing sequences. During amplification, additional probes that hybridize in a sequence-specific manner, like TaqMan, or additional primers that add specificity of amplification, may utilize these sequences to allow greater assurance of accurate amplification of the first complementary sequence to the target polynucleotide.

In other embodiments, the linker sequence comprises a region in common with all loop primers utilized in a reaction mixture. Such linker sequence common to all loop primers may reduce the cost of detection and quantitation, since subsequent probes (e.g. TaqMan probes), enzymatic digestion and its sequences, forward primers, and any other reagents acting on the loop primer can be versatile in use across many different loop primers used to detect many different target polynucleotides.

In some embodiments, each of a plurality of loop primers is designed such that the melting temperature of each loop primer or of each first complementary nucleic acid molecule is between 35° C. and 90° C., such as between 40° C. and 75° C., between 45° C. and 65° C., or between 50° C. and 55° C. In some embodiments, each of a plurality of loop primers is designed such that the melting temperature of each loop primer or of each complementary nucleic acid molecule is about, less than about, or more than about 40° C., 45° C., 50° C., 55° C., 60° C., 65° C., 70° C., 72° C., 75° C., 80° C., or more. In some embodiments, the first primer can be present at a concentration of about, at least about, or at most about 10, 50, 100, 150, 200, 250, 300, 350 to 300, 350, 400, 450, 500, 550, 600, 800, 10000 nM or µM, or any range or value derivable there between.

After producing the first complementary sequence using a loop primer and template-directed primer extension from Sequence B's 3' end, using the target polynucleotide as the template, this first complementary sequence becomes a template for amplification subsequent reactions, including for the purpose of quantification as well as detection. In order to generate additional copies the first complementary sequence, especially for regions within that are complementary to the target polynucleotide, a forward primer hybridizes specifically to a sequence within the linker sequence D and a reverse primer hybridizes specifically to a sequence more 5' than Sequence A' on the target polynucleotide, which would be more 3' than Sequence A on the first complementary sequence. This particular region, flanked by the selected primers, can then be amplified exponentially in subsequent reactions, much like conventional PCR.

In some embodiments, the method for producing a complementary sequence to a region in a target polynucleotide in a sample further comprises the step of amplifying the complementary sequence to a region in a target polynucleotide in a sample in the presence of a reverse primer and optionally a forward primer, wherein the reverse primer and the forward primer exhibit sequence complementarity to the amplified product and the loop primer, respectively. In some embodiments, the forward primer specifically hybridizes to a sequence in the linker sequence. In some embodiments, the reverse primer specifically hybridizes to a sequence that is complementary to a portion of the target polynucleotide that is 5' with respect to sequence A' or B'.

The forward and reverse primers are generally sufficiently long to prime the template-directed amplification of the target nucleic acid sequence under the conditions of the amplification reaction. The length of the second primer set primers will depend on many factors known in the art, such as the desired hybridization temperature of the primer, the target nucleic acid sequence, and the complexity of the different target nucleic acid sequences to be amplified. In some embodiments, the forward and reverse sequence comprises one or more nucleotide mismatches with the target sequence, such as 1, 2, 3, 4, 5, 6, 7, 8, 9, 10, or more mismatches. Selection of a substantially non-complementary sequence will depend on the target to be amplified. Such a substantially non-complementary sequence may be artificial or designed, such as a sequence found in another organism, a sequence found in another species, a sequence found in another sub-species, a substantially non-complementary sequence from a different member of the same species, a sequence from the same subject selected from a region substantially non-complementary to the target, a randomly generated sequence known to be substantially-non-complementary to the target, or a specifically designed sequence known to be substantially non-complementary to the target.

Where desired, the loop, forward, and reverse primers each may comprise a nucleotide analogue, such as a modified nucleic acid, or other non-canonical nucleotide. Other non-limiting examples of nucleotide analogues include but are not limited to 2-Aminopurine, 2,6-Diaminopurine, 5-Bromo dU, deoxyUridine, Inverted dT, dideoxy nucleotides, 5-Methyl dC, deoxyInosine, locked nucleic acids (LNAs), 5-Nitroindole, and 2'-O-Methyl RNA Bases.

In some embodiments, a forward and a reverse primer are designed such that the melting temperature of each is between 35° C. and 90° C., such as between 40° C. and 75° C., between 45° C. and 65° C., or between 50° C. and 55° C. In some embodiments, each of a plurality of forward and reverse primers is designed such that the melting temperature of each is about, less than about, or more than about 40° C., 45° C., 50° C., 55° C., 60° C., 65° C., 70° C., 72° C., 75° C., 80° C., or more. In further embodiments, the loop, forward, and reverse primers can be present in the amplification reaction at concentrations of about, at least about, or at most about 10, 50, 100, 150, 200, 250, 300, 350 to 300, 350, 400, 450, 500, 550, 600, 800, 10000 nM or μM, or any range or value derivable there between.

As noted above, in some embodiments, amplification of the first complementary nucleic acid molecule in a subject method is achieved through the use of the loop primer in combination with a second set of primers including a forward and a reverse primer disclosed herein. The second primer set can be added to the reaction at the same time as the loop primer. Alternatively, the second primer set is added after the extension of the loop primer. In still other embodiments, an additional amount of loop primer may be added following the extension reaction. Addition of an amount of loop primer following the extension reaction can be accompanied by the addition of a second primer set. In some embodiments, a forward primer (e.g. a primer that hybridizes to a complement of a sequence within the loop primer) is about or at least about 10, 15, 20, or more nucleotides in length. A forward primer may be designed to have a desired melting temperature, such as a Tm of between 55-75° C. (e.g. 62° C.). A reverse primer (e.g. a primer that hybridizes to a complement of a target polynucleotide, such as a miRNA) may be designed to have one or more properties, such as a Tm of between 55-75° C. (e.g. 62° C.).

In some embodiments, the reaction takes place in a single reaction mixture under conditions to yield the complete sequence to the region of the target polynucleotide, wherein the reaction mixture comprises: (a) the loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B and sequence B' on the target polynucleotide, wherein sequence A' and sequence B' are oriented 5' to 3' on the target polynucleotide; (b) the polymerase that extends sequence B of the loop primer from 5' to 3' along the target polynucleotide that serves as the template for a template-directed primer extension to produce the complementary sequence of the target polynucleotide; (c) the reverse primer that exhibits sequence homology to a sequence in the target polynucleotide located 5' with respect to sequence A' or B'; and, (d) the forward primer that specifically hybridizes to a sequence complementary to the loop primer.

In some embodiments, a subject method utilizes a loop, forward, and/or reverse primer present in excess as compared to the amount of the target polynucleotides. For example, the loop, forward and/or reverse primer utilized are least about 1-fold, 10-fold, 100-fold, 200-fold, 300-fold, 400-fold, 500-fold, 600-fold, 700-fold, 800-fold, 900-fold, 1000-fold, 1500-fold, 2000-fold, 3000-fold, 5000-fold, 7500-fold, 10000-fold, 20000-fold, 50000-fold, 100000-fold, $10^6$-fold, $10^7$-fold, $10^8$-fold, or more than the target polynucleotides present in the amplification reaction. In some embodiments, the use of the loop primer, a forward primer and a reverse primer permits amplification of one or more target nucleic acid molecules to a detectable level with fewer than about 5000, 2500, 1000, 900, 800, 700, 600, 500, 400, 300, 200, 100, 50, 40, 30, 20, 10, 5, or fewer copies of the one or more target nucleic acid molecules present in the sample prior to the amplification.

The production of the first complementary sequence can be part of a one-step RT-PCR or a two-step RT-PCR, wherein the reaction mixture may contain reagents separately for first-strand synthesis and amplification, or reagents for both first-strand synthesis and amplification together. Furthermore, the reaction mixture for subsequent amplification may contain different primers which hybridize to the first complementary sequence product, to yield products of different lengths or that covers different ranges within the first complementary sequence. Moreover, specific probes that quantitate or detect regions within the first complementary sequence may increase specificity; for example, TaqMan probes that recognize specific regions in the linker sequence D, target polynucleotide sequence, or even an overlap between those two regions in the first complementary sequence can be added in the reaction mixture prior to, concurrent with or subsequent to production of the first complementary sequence of a target nucleic acid.

The production of the first complementary sequence can be effected by polymerases. A wide variety of polymerases are available in the art. Non-limiting examples include an RNA-dependent DNA polymerase such as reverse transcriptases (RTs) derived from Moloney murine leukemia virus (MMLV-RT), avian myeloblastosis virus (AMV-RT), bovine leukemia virus (BLV-RT), Rous sarcoma virus (RSV-RT), human immunodeficiency virus (HIV-RT), rous associated virus (RAV-RT), myeloblastosis associated virus (MAV-RT) or other avian sarcoma-leukosis virus (ASLV-RT), *Thermus* Z05 polymerase, delta Z05 polymerase, and any modified versions or derivatives thereof. In some embodiments, the RNA-dependent DNA lacks RNaseH activity (e.g., SUPERSCRIPT III™ sold by Invitrogen, 1600 Faraday Avenue, PO Box 6482, Carlsbad, Calif. 92008). In some embodiments, the enzyme having RNA-dependent DNA polymerase activity also has DNA-dependent DNA polymerase activity, and is used for both reverse transcription and amplification steps.

Conditions for primer extension of the loop primer, in any one of the subject methods may vary depending on the target, the hybridization requirements of the first primer, the polymerase, requirements for other reagents, and the desired outcome. Methods for varying primer extension conditions are known in the art. A number of reagents are commercially available, and the concentrations can be optimized to achieve a desirable result. A non-limiting example of a typical reverse-transcription procedure includes the steps of primer extension carried out at about 42° C. for about 120 minutes and inactivating the enzyme by incubation at temperatures at or above about 80° C. for about 5 minutes. Incubation temperatures for extension may vary depending on the factors mentioned, and may include temperatures of about, more than about, or less than about 25° C., 30° C., 35° C., 40° C., 45° C., 48° C., 50° C., 52° C., 55° C., 60° C., 65° C., 70° C., 75° C., or any temperature there between. In some embodiments, the incubation temperature for the extension reaction is between 48° C. and 52° C. Incubation times for extension can also be varied to include times of about, more than about, or less than about 1, 2, 3, 4, 5, 10, 15, 20, 30, 40, 50, 60, 70, 80, 100, 120, 140, 180, or more minutes. Inactivation time and temperature can be any such that enzyme inactivation is achieved, and may include without limitation temperatures of about, more than about, or less than about 70° C., 75° C., 80° C., 85° C., 90° C., or 95° C. and times of about or more than about 1, 2, 3, 4, 5, 6, 7, 8, 9, 10, 15, 20, 30 or more minutes. Primer extension may or may not be preceded by a heat denaturation step to disrupt intermolecular and intramolecular interactions between RNA molecules. In some embodiments, primer extension is not preceded by a heat denaturation step. In some embodiments, the reverse transcription procedure does not include a heat inactivation step. In some embodiments the reverse transcription and PCR steps are integrated, being performed in a single tube. The reverse transcription may then be performed at ambient temperature, where the polymerase, which preferably is hot-start, has low activity. The reverse transcriptase is preferably native or engineered variants of Moloney murine leukemia virus (M-MLV) or avian myeloblastosis virus (AMV). It is also possible to perform the RT-PCR using a single enzyme, such as the Pyrophage (Lucigen Inc.), which has both activities.

Where desired, the first complementary nucleic acid molecules are enzymatically amplified using the polymerase chain reaction (PCR). This technique typically employs a DNA-dependent DNA polymerase, which is an enzyme capable of catalyzing polymerization of DNA. One application of this method is detecting or isolating nucleic acids present in low copy numbers. In certain aspects, a polymerase is active at about, or higher than about 20° C., 23° C., 25° C., 37° C., 42° C., 50° C., 60° C., 70° C., 80° C., 90° C. or higher. In some embodiments, the subject methods utilizes a thermostable polymerase. Exemplary thermostable polymerases include, but are not limited to, *Thermus thermophilus* HB8 (see e.g., U.S. Pat. No. 5,789,224 and U.S. publication 20030194726); mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y) (see e.g., U.S. Pat. No. 5,614,365), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* ZO5 polymerase; delta ZO5 polymerase (e.g. delta ZO5 Gold DNA polymerase); and mutants, variants, or derivatives thereof. Exemplary non-thermostable polymerases include, but are not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase. In some embodiments, the enzyme having DNA-dependent DNA polymerase activity used in the amplification step is the same enzyme used for primer extension of the first primer in the first primer extension step, such that the enzyme also has RNA-dependent DNA polymerase activity.

In some embodiments, a subject method utilizes a hot start polymerase. A hot start polymerase is a modified form of a DNA Polymerase that requires thermal activation (see for example U.S. Pat. Nos. 6,403,341 and 7,122,355, hereby incorporated by reference in their entirety). Such a polymerase can be used, for example, to further increase sensitivity, specificity, and yield; and/or to further improve low copy target amplification. Typically, the hot start enzyme is provided in an inactive state. Upon thermal activation the modification or modifier is released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Minis Bio; USB Corp.; Yorkshire Bioscience Ltd; and the like.

The subject methods can be utilized to simultaneously produce complementary sequences of different target polynucleotides with different sequences. The generation of more than one different first complementary nucleic acid molecule can be achieved through the use of more than one different loop primer in the extension reaction, each different loop primer having a different first sequence at its 3' end with complementarity to at least a portion of one of a plurality of different polynucleotide molecule targets. In some embodiments, these different loop primer sequences can be selected to have defined sequences with complementarity to at least a portion of specific polynucleotide molecule targets of interest. In other embodiments, the loop primer sequences are random and undefined, or near-random, with certain positions along the loop primer sequences biased toward one or more nucleotides, for example, comprising one or more nucleotides selected at random from two or more different nucleotides. A plurality of different loop primers can be combined, with concentrations of each of the different loop primers being the same or different, to create a "pool" of loop primers. Use of such a pool of loop primers allows for the simultaneous production of a plurality of different first complementary nucleic acid molecules, each with complementarity to one of a plurality of different polynucleotide molecule targets.

In a further embodiment in the methods, more than one different first complementary polynucleotide molecule is used as a template for amplification to produce multiple copies. This can be achieved through the use of more than one set of forward and reverse primers in the amplification reaction, each different primer having a different second sequence at its 3' end with complementarity to at least a portion of one of a plurality of different first complementary polynucleotide targets. In some embodiments, these different forward and reverse primers can be selected to have defined sequences with complementarity to at least a portion of specific first DNA molecule targets of interest. In other aspects, the different forward and reverse primers are random and undefined, or near-random, with certain positions along the sequences biased toward one or more nucleotides, such as one or more nucleotides selected at random from two or more different nucleotides. A plurality of different forward and reverse primers can be combined, with concentrations of each of the different primers being the same or different, to create a "pool" of secondary primers. Use of such a pool of secondary primers, in combination with a pool of loop primers, allows for the simultaneous production of a plurality of different first complementary sequence molecules, each with complementarity to at least a portion of one of a plurality of different target polynucleotide molecule targets.

Combinations of primers in pools for either the production or amplification of first DNA molecules can be any of a number of options. Production of first DNA molecules using a pool of first primers may be followed by amplification using one or more select second primers with second sequences having complementarity to one or more select first DNA molecules. Alternatively, production of first DNA molecules using a pool of first primers may be followed by amplification using a pool of second primers, wherein the pool contains a second primer for each of the intended first DNA molecule products of the primer extension reaction. In yet another embodiment, one or more pairs of first and second primers may be added to amplify one or more first DNA molecules produced by primer extension using a pool of first primers. Primer pools need not contain completely overlapping subsets of RNA and complementary first DNA molecule targets.

The subject method of producing complementary sequence to a target polynucleotide and/or amplification of the double-stranded target polynucleotide can be performed in the same reaction site (e.g., contained in a container). Reagents for producing the complementary sequence and the reagents for the subsequent amplification can be added simultaneously or sequentially. In some embodiments, all reagents for conducting both the loop primer extension reaction and the amplification reaction are added at once, such that both reactions can be carried out without further manipulation of the sample. In some embodiments, one or more reagents for conducting the amplification reaction are added after the loop primer extension reaction. In some embodiments, the amplification of a first complementary molecule is carried out in a separate container from that used in the production of the first DNA molecule by primer extension of a loop primer. When transferring the loop primer extension products, either the full reaction volume or a portion thereof may be used. Multiple portions from a single loop primer extension reaction may be transferred to multiple separate containers in order to conduct multiple amplification reactions. The separate reaction container may be of the same or different type as that used in the primer extension reaction. Non-limiting examples of reaction containers include microcentrifuge tubes, conical tubes, thin-walled tubes, strip tubes, multi-well plates, microfluidic devices, and microarrays.

Where desired, the various steps of the reaction can take place with one or more primers (e.g., loop primer, forward or reverse primer) being coupled to a support. In some embodiments, one or more loop primers are coupled to a solid support. In some embodiments, one or more of loop, together with a forward and a reverse primers are coupled to a support. Coupling can be achieved in a number of ways, non-limiting examples of which include covalent linkage, electrostatic interactions, and intermolecular interactions between two or more molecules. Different kinds of solid supports are known in the art, non-limiting examples of which include wafers, chips, beads, wells, plates, microfluidic devices, microarrays, and tubes of various sizes. Solid supports can be constructed of a variety of materials capable of supporting such couplings, non-limiting examples of which include silicon, plastics, glass, polymers, metals, and semi-conducting materials.

In practicing one or more subject methods, one may utilize reaction container that is designed to simultaneously amplify a plurality of different target polynucleotide molecules, each different target molecule being amplified in a distinct location. This can be achieved in a variety of ways. In one embodiment, each of a plurality of distinct locations comprises one or more primers with a second sequence complementary to at least a portion of a specific first complementary sequence molecule, such as in an array. Each of the distinct locations may further comprise a corresponding loop primer for the generation and amplification of the particular target polynucleotide. Primers may or may not be physically coupled to their respective distinct locations. Alternatively, beads coupled to one or more primers with a second sequence having complementarity to at least a portion of a particular first complementary sequence molecule are isolated in distinct locations from other beads being coupled to one or more second primers with a different second sequence, wherein isolation is achieved, for example, by lipid in water emulsion or arraying on a surface. In some embodiments, the production by primer extension of first complementary sequence molecules is done free in solution before amplification in distinct locations. In other embodiments, the production by primer extension of first complementary sequence molecules is carried out in distinct locations, such as when loop and second primer set of forward and reverse primers are located in distinct locations.

The amplification of a target nucleotide sequence or a region thereof can be performed with multiple cycles during a polymerase chain reaction. A desirable number of amplification cycles can be between one and 45 amplification cycles, such as from 1 to 25 amplification cycles, or such as from 5 to 35 amplification cycles, or such as 10 to 45 amplification cycles. Cycling parameters will vary, and may be optimized, based on a number of factors, including but not limited to, primer sequence, primer melting temperatures, length of target molecule, target sequence, complexity of target, complexity of target population, optimal activity of polymerase enzyme, and the requirements of other reagents. A non-limiting example of a typical PCR protocol is as follows: (1) 95° C. for 10 minutes, (2) 95° C. for 20 seconds, (3) 50° C. for 20 seconds, (4) 72° C. for 1 minute, (5) repeat steps 2 through 4 forty times, (6) 72° C. for 10 minutes, where steps (1) through (6) correspond to initial melting, cycle melting, hybridization, extension, cycle count, and final extension, respectively. The temperature and duration for each of the steps can be optimized for each reaction, as can the rate of temperature change from one step to the next. In some embodiments, it may be possible to combine step (3) (annealing) and step (4) (extension), and step (6) may be excluded altogether. A non-limiting example of such a PCR protocol is as follows: (1) 95° C. for 10 minutes, (2) 95° C. for 15 seconds, (3) 60° C. for 1 minute, (4) repeat steps 2 through 3 39 times. In some embodiments, the hybridization temperature is about, at least about, or at most about 20° C., 25° C., 30° C., 35° C., 40° C., 45° C., 50° C., 55° C., 60° C., 65° C., 70° C., 75° C., or more. In some embodiments, the duration of the hybridization step is about, at least about, or at most about 0, 1, 2, 3, 4, 5, 6, 7, 8, 9, 10, 15, 20, 30, 45, 60, 90, 120, or more seconds. In some embodiments, it may be desirable to include a melting curve analysis. A non-limiting example of melting curve analysis parameters is as follows: (1) 95° C. for 15 seconds, (2) 60° C. for 15 seconds, (3) 95° C. for 15 seconds.

The success of the amplification reaction can be determined by detecting amplification products during (e.g. in real-time) or after the amplification process through the use of detectable markers, such as probes or labels. For example, the amplified DNA molecules can be detected and quantified by the presence of a dye (e.g., SYBR green) that preferentially or exclusively binds to double stranded DNA during the PCR amplification step of the methods of the present invention. For example, Molecular Probes, Inc. (29851 Willow Creek Road, Eugene, Oreg. 97402) sells quantitative PCR reaction mixtures that include SYBR green dye. By way of further example, another dye (referred to as "BEBO") that can be used to label double stranded DNA produced during real-time PCR is described by Bengtsson, M., et al., Nucleic Acids Research 31(8):e45 (Apr. 15, 2003), which publication is incorporated herein by reference. By way of example, a first and/or second primer that includes a fluorophore and quencher can be used to prime the PCR amplification step of the methods of the present invention. The physical separation of the fluorophore and quencher that occurs after extension of the labeled primer during PCR permits the fluorophore to fluoresce, and the fluorescence can be used to measure the amount of the PCR amplification products. Examples of commercially available primers that include a fluorophore and quencher include Scorpion primers and Uniprimers, which are both sold by Molecular Probes, Inc.

In some embodiments, oligonucleotide probes present in a multiplex amplification are suitable for monitoring the amount of amplification product produced as a function of time. Such oligonucleotide probes include, but are not limited to, the 5'-exonuclease assay (e.g., TaqMan™) probes (see above and also U.S. Pat. No. 5,538,848), stem-loop molecular beacons (see, e.g., U.S. Pat. Nos. 6,103,476 and 5,925,517 and Tyagi & Kramer, 1996), stemless or linear beacons (see, e.g., WO 99/21881), PNA Molecular Beacons (see, e.g., U.S. Pat. Nos. 6,355,421 and 6,593,091), linear PNA beacons (see, e.g. Kubista et al., 2001), non-FRET probes (see, e.g., U.S. Pat. No. 6,150,097), Sunrise®™/Amplifluor®™ probes (see, e.g., U.S. Pat. No. 6,548,250), stem-loop and duplex Scorpion™ probes (see, e.g., Solinas et al., 2001 and U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse™ probe (Epoch Biosciences), hairpin probes (see, e.g., U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001; Whitcombe et al., 1999; Isacsson et al., 2000; Svanvik et al., 2000; Wolffs et al., 2001; Tsourkas et al., 2002; Riccelli et al., 2002; Zhang et al., 2002; Maxwell et al., 2002; Broude et al., 2002; Huang et al., 2002; and Yu et al., 2001.

In certain embodiments, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody/antigen, ionic complexes, hapten/ligand (e.g., biotin/avidin). In still other aspects, use of labels can be accomplished using any one of a large number of known techniques employing known labels, linkages, linking groups, reagents, reaction conditions, and analysis and purification methods.

Further non-limiting examples of labels include light-emitting, light-scattering, and light-absorbing compounds which generate or quench a detectable fluorescent, chemiluminescent, or bioluminescent signal (see, e.g., Kricka, 1992) and Garman, 1997). Fluorescent reporter dyes useful as labels include, but are not limited to, fluoresceins (see, e.g., U.S. Pat. Nos. 5,188,934; 6,008,379; and 6,020,481), rhodamines (see, e.g., U.S. Pat. Nos. 5,366,860; 5,847,162; 5,936,087; 6,051,719; and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863,727; 5,800,996; and 5,945,526), and cyanines (see, e.g., Kubista, WO 97/45539), as well as any other fluorescent moiety capable of generating a detectable signal. Examples of fluorescein dyes include, but are not limited to, 6-carboxyfluorescein; 2',4',1,4,-tetrachlorofluorescein; and 2',4',5 ',7',1,4-hexachlorofluorescein. In certain aspects, the fluorescent label is selected from SYBR®-green, 6-carboxyfluorescein ("FAM"), TET, ROX, VIC™, and JOE. In certain embodiments, a label is a radiolabel.

In still a further embodiment, labels are hybridization-stabilizing moieties which serve to enhance, stabilize, or influence hybridization of duplexes, e.g., intercalators and intercalating dyes (including, but not limited to, ethidium bromide, EvaGreen®, and SYBR® green), minor-groove binders, and cross-linking functional groups (see, e.g., Blackburn, G. and Gait, M. Eds. "DNA and RNA structure" in Nucleic Acids in Chemistry and Biology (1996). Labels include those labels that effect the separation or immobilization of a molecule by specific or non-specific capture, for example biotin, digoxigenin, and other haptens (see, e.g., Andrus, 1995).

In some embodiments, different probes comprise detectable and different labels that are distinguishable from one another. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054 and Saiki et al., 1986.

In some embodiments, a detectable marker is used to determine the presence, absence, relative abundance, and/or quantity of a target nucleic acid molecule after the completion of an amplification reaction. In some embodiments, the detectable marker is a probe. In some embodiments, a plurality of different probes is used to simultaneously detect a plurality of different target nucleic acid molecule amplification products. The probes can be bound to a solid surface, such as on a bead or an array. Probes on an array can be arranged such that the location of each probe is known and that detection of hybridization of an amplification product to the probe identifies the amplification product. Examples of probes and arrays useful in the detection and/or quantification of non-coding RNA molecules are provided in US20080045418 and US20080312099, incorporated herein by reference.

The methods disclosed herein are applicable for producing complementary sequence of any types of target nucleic acid molecules, including but not limited to DNA. In some embodiments, the target polynucleotide is an RNA molecule. In some embodiments, the target polynucleotide is a non-coding RNA molecule. In some embodiments, the non-coding RNA molecule is selected from the group consisting of: a mature microRNA molecule, a pre-microRNA molecule, a primary microRNA molecule, an siRNA molecule, a piRNA molecule, a piwiRNA, a lncRNA, an rRNA, and an shRNA molecule. In some embodiments, the target polynucleotide is less than 100 nt in length. In some embodiments, the target polynucleotide is less than 50 nt in length.

Non-coding RNA molecules useful as targets for amplification in any of the disclosed methods can be isolated from any organism, for example a eukaryote, or a part thereof, including organs, tissues, and/or individual cells, including cultured cells. Any suitable preparation that includes a target RNA can be used, such as total RNA, purified small RNA, or samples containing both RNA and DNA. RNA can be isolated from cells by procedures that involve lysis of the cells, and may further involve denaturation of the proteins contained therein. Cells from which RNA is extracted may be wild-type cells, manipulated wild-type cells, modified cells, and manipulated modified cells, wherein manipulation includes, but is not limited to, drug treatment.

Short DNA molecules useful as targets for amplification in the methods of the invention can be isolated from any organism, for example a eukaryote, or a part thereof, including organs, tissues, and/or individual cells, including cultured cells using additional standard steps known in the art to remove some or all of the DNA. Procedures for cell lysis and nucleic acid extraction are well known in the art. Non-limiting examples of such procedures include the following. Cell lysis can be accomplished with, for example, a non-ionic detergent, followed by microcentrifugation to remove the nuclei and hence the bulk of the cellular DNA. RNA can be extracted from cells of the various types of interest using guanidinium thiocyanate lysis followed by CsCl centrifugation to separate the RNA from DNA (see Chirgwin et al., 1979, Biochemistry 18:5294-5299). Extraction of RNA, and optional isolation from DNA, can also be accomplished by organic extraction, for example, with phenol, phenol/chloroform/isoamyl alcohol, or similar formulations, including TRIzol (Invitrogen) and TriReagent (Applied Biosystems). Other non-limiting examples of extraction techniques include: (1) organic extraction followed by ethanol precipitation, e.g., using a phenol/chloroform organic reagent (Ausubel et al., 1993), in certain embodiments, using an automated nucleic acid extractor, e.g., the Model 341 DNA Extractor available from Applied Biosystems (Carlsbad, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. In certain embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell types, it may be desirable to add a protein denaturation/digestion step to the protocol. Samples containing RNA can comprise a multiplicity of different RNA molecules, each different RNA molecule having a different nucleotide sequence.

The subject method is particularly useful for amplifying short target sequences including short RNA molecules. The loop primer, with the added length of linker sequence D, adds length to the first complementary sequence for subsequent amplification. In some embodiments, the target polynucleotide is less than 100 nt, 90 nt, 80 nt, 70 nt, 60 nt, 50 nt, 40 nt, 30 nt, 20 nt, or 15 nt in length.

Compositions:

In another aspect, the present invention provides a composition for producing a complementary sequence to a region in a target polynucleotide in a sample, the composition comprising a loop primer, a forward primer, and a reverse primer, wherein: (a) the loop primer that comprises sequence A, a linker sequence, and sequence B, oriented from 5' to 3' on a single strand; wherein the loop primer specifically hybridizes to the target polynucleotide via (i) sequence complementarity between sequence A and sequence A' on the target polynucleotide, and (ii) sequence complementarity between sequence B and sequence B' on the target polynucleotide, wherein sequence A' and sequence B' are oriented 5' to 3' on the target polynucleotide; (b) the reverse primer that exhibits sequence homology to a sequence in the target polynucleotide located 5' with respect to sequence A'; and (c) the forward primer that specifically hybridizes to a sequence in the linker sequence.

The loop primer embodied in the subject composition can be any loop primer having one or more characteristics disclosed in the section above. For example, a loop primer comprises two stretches of complementarity to the target polynucleotide at its two ends. Sequence A used in the composition is the complementary stretch at the loop primer's 5' end, and Sequence B used in the composition is the complementary stretch at the loop primer's 3' end. These two sequences, used in the composition, basepair to sequences A' and B' of the target polynucleotide, where A' is positioned more 5' than B'. In another example, sequences A' and B' are very close to each other, and they are separated only by a sequence of N' on the target polynucleotide. In other embodiments, sequence A and A' can be at least 2, 3, 4, 5, 6, 7, 8, 9, or 10 nucleotides. In other examples, sequence B and B' can be at least 5, 6, 7, 8, 9, 10, 11, 12, 13, 14, 15, 16, 17, 18, 19, or 20 nucleotides. Sequence N' can be 1, 2, 3, 4, or 5 nucleotides.

Where desired, the loop primer may comprise any other features disclosed in the section above. For example, it may be desirable to design A' and B' regions residing close to the 3' end of the target polynucleotide. Such a selection ensures that sufficient number of target polynucleotide sequences are 5' of the A-A' and B-B' hybridization to be included in the first complementary sequence. For example, sequence A is about 2 nt to about 10 nt or 2 nt to about 5 nt, in length and sequence B is about 2 nt to about 10 nt in length or 2 nt to about 5 nt in length. In some embodiments, the combined length of sequences A and B is about 5 nt to about 20 nt, or 5 nt to about 15 nt, or 5 nt to about 10 nt. In some embodiments, the combined length of sequences A and B is sufficient to specifically hybridize to the target polynucleotide to effect the extension of the loop primer. In some embodiments, a linear concatenation of sequences B and A is at least 80%, 85%, 90%, 95%, 99% or 100% complementary to a linear concatenation of sequences A' and B' when optimally aligned. In some embodiments, a linear concatenation of sequences B and A is at least 90%, 95%, 99% or 100% complementary to a linear concatenation of sequences A' and B'. In some embodiments, the 3' end of sequence A' is within 1 nt to about 5 nt of sequence B'.

In some embodiments, the number of nucleotides in Sequence B can be greater than the number of nucleotides in Sequence A to increase the efficiency such that the A-A' hybridization is knocked off during the elongation of the primer-extension from the 3' end of Sequence B. In some embodiment, Sequence A and B are of equal length in nucleotide bases, comprising at least 3, 4, 5, 6, 7, 8, 9 or 10, but no more than about 50 nucleotides. In another embodiment, Sequence A is 2 nucleotides and Sequence B is 3 nucleotides. In another embodiment, Sequence A is 2 nucleotides and Sequence B is 4 nucleotides. In another embodiment, Sequence A is 3 nucleotides and Sequence B is 4 nucleotides.

The number of nucleotides in between Sequences A and B in the loop primer generally corresponds to the length of sequence N' and N, which may affect the efficiency of the polymerase extension at the 3' end of Sequence B during the first complementary strand synthesis. In some embodiments, the 3' end of sequence A' is within 1 nt to about 10 nt, within 1 nt to about 5 nt, or within 2 nt to about 5 nt, of the 5' end of sequence B'.

In some embodiment, loop primers are designed to detect single nucleate variation. For example, a pair of loop primers that differ in one base position in sequences A and B, such that one recognizes one allele of the target sequence and the other recognizes a different allele of the target sequence. The loop primers differ also in the loop sequence D and can be amplified and/or detected selectively.

The linker sequence D in a subject loop primer is generally designed to have a sufficient length for hybridization of both A-A' and B-B', which in turn increases the specificity of the loop primer in binding to the correct small RNA target. In one embodiment, the linker sequence is from about 5 to about 100, 10 to about 80, or 20 to about 50 nucleotides. In some other embodiments, the linker sequence is about 10, 20, 30, 40, 50, 60, 70, 80, 90 or about 100 nucleotides in length.

Where desired, the linker sequence used in the subject methods or present in the subject compositions comprises one or more sequence elements selected from the group consisting of: one or more barcode sequences, one or more restriction enzyme recognition sequences, one or more oligonucleotide probe binding sequences or complements thereof, one or more sequencing primer annealing sequences or complements thereof, and a combination of these. In some embodiments, the linker sequence comprises a universal sequence common to multiple different loop primers.

In some embodiments, the linker sequence comprises unique sequences to aid in the subsequent detection, quantitation of the produced complementary sequence of the target polynucleotide of interest. After producing the first complement sequence, portions of the linker sequence is complementary to the forward primer. Therefore, having specific barcodes within the linker sequence may allow different loop primers to be amplified, detected, or quantitated by different forward but the same reverse primers. In some embodiments, one loop primer's sequence A and B may bind to slightly different regions of the same target polynucleotide than another loop primer's sequence A and B, which allows greater specificity and/or user verification. Subsequent amplification, detection, and quantitation of these different loop primers can be facilitated by different forward primers binding differently due to different barcodes in the linker sequence.

In some embodiments, the linker comprises one or more restriction enzyme recognition sequences. After amplification, the accuracy of the detection can be markedly improved with a restriction digest, so that only genuine products amplified from the first complement sequence, containing the linker sequence restriction site, is cleaved and tabulated for detection and quantitation.

In other embodiments, the linker sequence comprises one or more oligonucleotide probe binding sequences, complements of oligonucleotide probe binding sequences, primer annealing sequences, or complements of primer annealing sequences. During amplification, additional probes that hybridize in a sequence-specific manner, like TaqMan, or additional primers that add specificity of amplification, may utilize these sequences to allow greater assurance of accurate amplification of the first complementary sequence to the target polynucleotide.

In other embodiments, the linker sequence comprises a region in common with all loop primers utilized in a reaction mixture. Such linker sequence common to all loop primers may reduce the cost of detection and quantitation, since subsequent probes (e.g. TaqMan), enzymatic digestion and its sequences, forward primers, and any other reagents acting on the loop primer can be versatile in use across many different loop primers used to detect many different target polynucleotides.

In some embodiments, the subject composition is prepared in a dehydrated form. In some embodiments, the subject composition is packaged in a container. For example, the container can be a well, a plate, a tube, a chamber, a flask, a bottle, syringe, a flow cell, a chip or the like.

In some embodiments, the subject composition is packaged as a kit containing any one or more of the elements disclosed in the above methods, compositions, reaction mixtures, tests, and/or systems. In some embodiments, a kit comprises a composition of the invention, in one or more containers. For example, kits may include one or more of the following: one or more solid supports comprising oligonucleotides attached thereto, one or more oligonucleotides for attachment to a solid support, one or more loop primers, one or more amplification primers, reagents for utilizing any of these, and instructions for using any of these. In some embodiments, the kit further comprises one or more of: (a) a DNA ligase, (b) a DNA-dependent DNA polymerase, (c) an RNA-dependent DNA polymerase, (d) random primers, (e) dependent DNA polymerase having 3' to 5' exonuclease activity, (f) a plurality of primers, each primer having one of a plurality of selected sequences, (g) a DNA kinase, (h) a DNA exonuclease, (i) magnetic beads, and (j) one or more buffers suitable for one or more of the elements contained in the kit. The primers, other oligonucleotides, and reagents can be, without limitation, any of those described herein. Elements of the kit can further be provided, without limitation, in any amount and/or combination (such as in the same kit or same container). The kits may further comprise additional agents for use according to the methods of the invention. The kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

In one embodiment, the kit may comprise a reaction mixture comprising one or more of the following components: a target polynucleotide, a loop primer disclosed herein, a forward primer, a reverse primer, and a polymerase to yield a detectable amount of an amplicon, wherein the target polynucleotide is less than about 100 nt in length.

Where desired, the components of a subject kit may be packaged either in aqueous media or in lyophilized form, in a container. Where there is more than one component in the kit, the kit also will generally contain a second, third or other additional container into which the additional components may be separately placed. However, various combinations of components may be comprised in one or more vials. The kits of the present invention also will typically include a container for containing primers, probes, buffer, diluent and/or any other reagent containers in close confinement for commercial sale. Such containers may include injection or blow molded plastic containers into which the desired vials are retained. When the components of the kit comprising the composition for producing a complementary sequence to a region in a target polynucleotide are provided in one or more liquid solutions, the liquid solution is typically an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

In some embodiments, a subject kit includes instructions to users as to how to use the kit components to produce a complementary sequence to a region in a target polynucleotide.

Where desired, a subject kit can further comprise one or more detectable markers to enable monitoring of accumulation of amplification products, such as in real-time. Non-limiting examples of detectable markers are described above and include dyes, such as SYBR green dye or BEBO dye, that preferentially or exclusively bind to double stranded DNA during a PCR amplification step. In other embodiments, the kit may include a first and/or second primer that includes a fluorophore and quencher to measure the amount of the PCR amplification products. It some embodiments, the kit further comprises a probe of any of the kinds described above to detect the progress or products of an amplification reaction.

A subject kit can further comprise one or more reagents necessary for producing a complementary sequence to a region in a target polynucleotide. For example, a kit may comprise any RNA dependent DNA polymerase that can be used to synthesize the first DNA molecules. Non-limiting examples of RNA dependent DNA polymerases include reverse transcriptases (RTs) derived from Moloney murine leukemia virus (MMLV-RT), avian myeloblastosis virus (AMV-RT), bovine leukemia virus (BLV-RT), Rous sarcoma virus (RSV-RT), human immunodeficiency virus (HIV-RT), rous associated virus (RAV-RT), myeloblastosis associated virus (MAV-RT) or other avian sarcoma-leukosis virus (ASLV-RT), *Thermus* Z05 polymerase, delta Z05 polymerase, and any modified versions or derivatives thereof. In some embodiments, the RNA-dependent DNA lacks RNaseH activity (e.g., SUPERSCRIPT III™ sold by Invitrogen, 1600 Faraday Avenue, PO Box 6482, Carlsbad, Calif. 92008). In some embodiments, the enzyme having RNA-dependent DNA polymerase activity also has DNA-dependent DNA polymerase activity, and is used for both reverse transcription and amplification steps in the reaction mixture.

In another aspect, the present invention provides a reaction mixture for producing a complementary sequence to a region in a target polynucleotide in a sample, the reaction mixture comprising a loop primer, a forward primer, and a reverse primer, wherein: (a) the loop primer that comprises sequence A, a linker sequence, and sequence B, oriented from 5' to 3' on a single strand; wherein the loop primer specifically hybridizes to the target polynucleotide via (i) sequence complementarity between sequence A and sequence A' on the target polynucleotide, and (ii) sequence complementarity between sequence B and sequence B' on the target polynucleotide, wherein sequence A' and sequence B' are oriented 5' to 3' on the target polynucleotide; (b) the reverse primer that exhibits sequence homology to a sequence in the target polynucleotide located 5' with respect to sequence A'; and (c) the forward primer that specifically hybridizes to a sequence in the linker sequence.

The target polynucleotide used in the reaction mixture may be a short non-coding RNA or any other short RNA, including a microRNA, or any other target polynucleotides described in the method section above. Similarly, any loop primer disclosed herein can be used in a reaction mixture. The choice of the particular sequence of the loop primer will depend on the target polynucleotide sequence to be generated.

The reaction mixture may comprise reagents necessary for producing a complementary sequence to a region in a target polynucleotide in sample, including enzymes, buffers and the like. For example, the reaction mixture may comprise any RNA dependent DNA polymerase that can be used to synthesize the first DNA molecules. Non-limiting examples of RNA dependent DNA polymerases include reverse transcriptases (RTs) derived from Moloney murine leukemia virus (MMLV-RT), avian myeloblastosis virus (AMV-RT), bovine leukemia virus (BLV-RT), Rous sarcoma virus (RSV-RT), human immunodeficiency virus (HIV-RT), rous associated virus (RAV-RT), myeloblastosis associated virus (MAV-RT) or other avian sarcoma-leukosis virus (ASLV-RT), *Thermus* Z05 polymerase, delta Z05 polymerase, and any modified versions or derivatives thereof. In some embodiments, the RNA-dependent DNA lacks RNaseH activity (e.g., SUPERSCRIPT III™ sold by Invitrogen, 1600 Faraday Avenue, PO Box 6482, Carlsbad, Calif. 92008). In some embodiments, the enzyme having RNA-dependent DNA polymerase activity also has DNA-dependent DNA polymerase activity, and is used for both reverse transcription and amplification steps in the reaction mixture.

In some embodiments, the reaction mixture of the present invention further comprises buffers with a potassium salt (e.g., potassium chloride), a magnesium salt (e.g., magnesium chloride), a reducing agent (e.g., dithiothreitol), deoxynucleoside triphosphates (dNTPs), detergent, nucleotides or nucleotide analogs, and one or more detectable markers for monitoring accumulation of amplification products in real time.

In some embodiments, the reaction mixture for producing a complementary sequence to a region in a target polynucleotide in a sample is in a container disclosed herein. In some embodiments, the container is a well, a plate, a tube, a chamber, a flow cell, or a chip.

The subject methods and compositions are particularly useful for producing and amplifying cDNA molecules from small nucleic acid target molecules, such as from miRNA molecules. The amount of the DNA molecules can be measured which can provide a measurement of the amount of target small nucleic acid molecules in the starting material. For example, the methods, compositions, reaction mixtures, tests, kits, and/or systems of the present invention can be used to measure the amount of specific non-coding RNA molecules (e.g., specific miRNA molecules) in living cells. For example, the present invention can be used to measure the amount of specific non-coding RNA molecules (e.g., specific miRNA molecules) in different cell types in a living body, thereby producing an "atlas" of the distribution of specific non-coding RNA molecules within the body. In addition, the present invention can be used to measure changes in the amount of specific non-coding RNA molecules (e.g., specific miRNA molecules) in response to a stimulus, such as in response to treatment of a population of living cells with a drug.

Embodiments of the invention's methods, compositions, reaction mixtures, tests, kits, and/or systems can be useful for diagnosing and/or assessing a condition or potential condition in a patient comprising measuring expression of one or more small nucleic acids, such as a miRNA, in a sample from a patient. A difference in the expression in the sample from a patient and a reference, such as expression in a normal or non-pathologic sample, may be indicative of a pathologic, disease, or cancerous condition, or risk thereof. A sample may be taken from a patient having or suspected of having a disease or pathological condition. In certain aspects, the sample can be, but is not limited to tissue (e.g., biopsy, particularly fine needle biopsy), blood, serum, plasma, pancreatic juice, or other bodily fluids. The sample can be fresh, frozen, fixed (e.g., formalin fixed), embedded (e.g., paraffin embedded), or a combination of these (e.g. formalin fixed and paraffin embedded).

The present invention's methods, compositions, reaction mixtures, tests, kits, and/or systems are of particular interest in the diagnostic screening of small nucleic acid samples for many diseases or conditions. In certain embodiments, diagnostic methods involve identifying one or more RNA, such as miRNAs, differentially expressed in a sample that are indicative of a disease or condition (non-normal sample). In certain embodiments, diagnosing a disease or condition involves detecting and/or quantifying an expressed non-coding RNA (and optionally one or more coding RNAs). In some embodiments, the methods of the invention are used to compare the presence, absence, relative abundance, and/or quantity of non-coding RNAs between one or more samples related to a condition and one or more samples not related to a condition, and thereby establish correlations between the presence, absence, relative abundance, and/or quantity of one or more non-coding RNAs and the condition. RNAs correlated with a disease phenotype are referred to as "biomarkers." In certain embodiments, the invention provides for the detection of amplicons that are shorter (e.g. <30 nt) than by traditional quantitative reverse-transcriptase PCR (qRT-PCR) methods that rely on longer amplicons (e.g. 60-200 nt). Clinical samples are often subject to extensive RNA degradation, which can limit the sensitivity of detection if the amplicon size of the target is approximately the same size as the degraded RNA or larger. The use of shorter amplicons to detect the target improves the likelihood that the target will be exponentially amplified even if highly degraded. Moreover, the use of shorter target-specific amplicons to detect RNA can offer sensitive quantification of RNA in formalin fixed paraffin embedded (FFPE) samples, where the RNA can be compromised by covalent modifications through the fixation process, as well as degraded by the high temperatures used in the embedding process.

The invention may also be used for the detection of nucleic acids in infectious disease, such as RNA viruses such as HIV, HCV, and other microbes. The invention may also have utility for the detection of disease specific non-coding RNA in diseases such as leukemia, where the knowledge of the precise biomarker can have prognostic value, as well as guide therapeutic decision-making and other aspects of disease management, such as predicting responsiveness to a selected treatment.

Particularly, the methods, compositions, reaction mixtures, tests, kits, and/or systems of the present invention can be used to evaluate samples with respect to diseases or conditions that include, but are not limited to: Alzheimer's disease, macular degeneration, chronic pancreatitis; pancreatic cancer; AIDS, autoimmune diseases (rheumatoid arthritis, multiple sclerosis, diabetes—insulin-dependent and non-independent, systemic lupus erythematosus and Graves disease); cancer (e.g., malignant, benign, metastatic, precancer); cardiovascular diseases (heart disease or coronary artery disease, stroke-ischemic and hemorrhagic, and rheumatic heart disease); diseases of the nervous system; and infection by pathogenic microorganisms (Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis); inflammation (allergy, asthma); prion diseases (e.g., CJD, kuru, GSS, FFI).

Cancers that may be evaluated by the methods, compositions, reaction mixtures, tests, kits, and/or systems of the present invention include cancer cells that include cells and cancer cells from the bladder, blood, bone, bone marrow, brain, breast, colon, esophagus, gastrointestine, gum, head, kidney, liver, lung, nasopharynx, neck, ovary, pancreas, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, RNA can be evaluated in pre-cancers, such as metaplasia, dysplasia, and hyperplasia.

It is specifically contemplated that the present invention can be used to evaluate differences between stages of disease, such as between hyperplasia, neoplasia, pre-cancer and cancer, or between a primary tumor and a metastasized tumor. Moreover, it is contemplated that samples that have differences in the activity of certain pathways may also be compared. These pathways include the following and those involving the following factors: antibody response, apoptosis, calcium/NFAT signaling, cell cycle, cell migration, cell adhesion, cell division, cytokines and cytokine receptors, drug metabolism, growth factors and growth factor receptors, inflammatory response, insulin signaling, NFκ-B signaling, angiogenesis, adipogenesis, cell adhesion, viral infection, bacterial infection, senescence, motility, glucose transport, stress response, oxidation, aging, telomere extension, telomere shortening, neural transmission, blood clotting, stem cell differentiation, G-Protein Coupled Receptor (GPCR) signaling, and p53 activation.

Cellular pathways that may be assessed using the methods, compositions, reaction mixtures, tests, kits, and/or systems of the present invention also include, but are not limited to, the following: an adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC 1, myosin light chain kinase, platelet-derived growth factor receptor or ezrin; any apoptosis pathway including, but not limited to, those involving AKT, Fas ligand, NFκB, caspase-9, PI3 kinase, caspase-3, caspase-7, ICAD, CAD, EndoG, Granzyme B, Bad, Bax, Bid, Bak, APAF-1, cytochrome C, p53, ATM, Bcl-2, PARP, Chk1, Chk2, p21, c-Jun, p'73, Rad51, Mdm2, Rad50, c-Abl, BRCA-1, perforin, caspase-4, caspase-8, caspase-6, caspase-1, caspase-2, caspase-10, Rho, Jun kinase, Jun kinase, R1p2, lamin-A, lamin-B1, lamin-B2, Fas receptor, H2O2, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, 111313 or the proteasome; any cell activation pathway including, but not limited to, those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, IKKα, IKKβ, NFκB, TRAF2, TRAF3, TRAF5, TRAF6, IL-4, IL-4 receptor, CDK5, AP-1 transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p2'7, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-1, BRCA-2, SKP1, the proteasome, CUL1, E2F, p107, steroid hormones, steroid hormone receptors, IκBα, IκKβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crm1, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKβ, NFκB, RAC1, RAF1, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-1 receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a non-coding RNA may be differentially expressed with respect to one or more of the above pathways or factors.

Phenotypic traits also include characteristics such as longevity, morbidity, appearance (e.g., baldness, obesity), strength, speed, endurance, fertility, susceptibility or receptivity to particular drugs or therapeutic treatments (drug efficacy), and risk of drug toxicity. Samples that differ in these phenotypic traits may also be evaluated using the methods described.

In certain embodiments of the methods, compositions, reaction mixtures, tests, kits, and/or systems of the present invention, nucleic acid profiles may be generated to evaluate and correlate those profiles with pharmacokinetics. For example, RNA profiles may be created and evaluated for patient tumor and blood samples prior to the patient's being treated or during treatment to determine if there are RNAs whose expression correlates with the outcome of the patient. Identification of differential RNAs can lead to a diagnostic assay involving them that can be used to evaluate tumor and/or blood samples to determine what drug regimen the patient should be provided. In addition, the methods can be used to identify or select patients suitable for a particular clinical trial. If a RNA profile is determined to be correlated with drug efficacy or drug toxicity, that may be relevant to whether that patient is an appropriate patient for receiving the drug or for a particular dosage of the drug.

In another aspect, the present invention provides a system for detecting a target polynucleotide in a sample, the system comprising: (a) a computer configured to receive a customer request to perform a detection reaction on a sample; (b) an amplification system that performs a nucleic acid amplification reaction in a reaction mixture disclosed herein to produce an amplified product; and, (c) a report generator that sends a report to a recipient, wherein the report contains results for detection of a detection signal corresponding to amount of the amplified product. In one embodiment, the recipient is the customer. In some embodiments, a computer-readable medium comprising of codes that, upon execution by one or more processors, implement a method of detecting a target polynucleotide in a sample, the method comprising: (a) receiving a customer request to perform a detection reaction on a sample; (b) performing a nucleic acid amplification reaction in a reaction mixture disclosed herein to produce an amplified product; and, (c) generating a report containing results for detection of a detection signal corresponding to amount of the amplified product.

In some embodiments the system further comprises a webpage configured to accept an offer to purchase a nucleic acid detection, quantitation, or amplification service. In some embodiments the display is electronic, for example, a webpage. In some embodiments the system further comprises a display that displays referrals to a counselor and/or other medical professional (for example, medical geneticists or obstetrician/gynecologist) based on the vended information.

The internet and the world wide web offer access to and distribution of information. In some embodiments, a website can be particularly suited to efficiently providing various functionality for allowing customers to purchase a nucleic acid detection, quantitation, or amplification service. The system typically will include a server on which the website resides. Users use an interface connected to the server, such as a computer monitor or a telephone screen, to interact with the website by clicking or rolling over links that pop up information or direct the user to another webpage. Websites typically are interactive, allowing the user to input information or a query and obtain a response on the interface.

In some embodiments of a system and business method, a website can allow a customer to purchase, manage, and view the results of nucleic acid detection, quantitation, or amplification, as well as to learn more generally about the consequences of these results. For example, a customer can be a patient who seeks to learn whether his or her small RNA profile is indicative of a disease profile. A customer can be presented with the offer to purchase nucleic acid detection, quantitation, or amplification service to determine one or more of: (i) the genetic status of the customer; (ii) the likelihood that the customer will develop one or more diseases or traits; and (iii) the probability that the customer will develop one or more diseases or traits, based on causal genetic variants identified in the customer's nucleic acid sample.

If the customer chooses to purchase nucleic acid detection, quantitation, or amplification service using the methods, compositions, reaction mixtures, tests, kits, and/or systems of the present invention, then the customer may pay a fee, for example through an online credit card transaction, in exchange for services, direct phone consultation with the company's staff and/or referrals to relevant medical professionals. The testing and referrals can be paid for by a fee at the point of purchase or can be included in an initial user registration fee. In some embodiments, the services are free and revenue is generated by the company by advertising other products in conjunction with a particular product. For example, after a customer places an order online, the order is sent to a server for processing. Once payment has been verified, the order processing server can send an electronic notification to a shipping vendor to mail a nucleic acid collection kit to the customer. In an embodiment, the collection kit is separate from the detection, quantitation, and/or amplification service, or the user or customer already has or obtains the nucleic acid collection kit from another source. Notifications can also periodically be sent electronically to the customer comprising order confirmation and updates on order and shipping status. In some embodiments of a business method of the invention, a customer can deposit a sample into the collection kit. Any sample that would be obvious to one skilled in the art can be deposited into or onto a collection kit. A sample can be any material containing nucleic acid to be analyzed that would be obvious to one skilled in the art, such as bodily fluid like saliva or blood. The collection kit can then be returned to the company for sending to a lab or can be returned directly to a lab for processing. A lab, either internal within the company, contracted to work with the company, or external from the company, can isolate the customer's nucleic acids from the provided sample. After the nucleic acids have been isolated from the sample, a device (such as an apparatus described herein) can be used to detect, amplify, and/or quantitate their presence. In some embodiments, the nucleic acid does not have to be isolated from the sample to detect, quantitate, and/or amplify the nucleic acids.

Information regarding the nucleic acids detected, quantitated, and/or amplified using the methods, compositions, reaction mixtures, tests, kits, and/or systems can be sent electronically to a server for storage and processing. Computer code on the server can execute on the nucleic acid information to infer the healthcare informatics of the customer and/or to confirm the presence of causal genetic variants and/or non-subject sequences, if any. The processed nucleic acid information can then be electronically sent to a server, where computer code on the server can execute on the processed nucleic acid information to predict the probability that the customer will have each of a plurality of traits caused by causal genetic variants found to be present in the customer's processed nucleic acid information. Results can then be electronically transmitted to a server for storage.

In an example, a notification can be sent to the customer to alert the customer to the availability of the results. The notification can be electronic, non-limiting examples of which include a text message, an email, or other data packet; or the notification can be non-electronic, non-limiting examples of which include a phone call from a counselor or printed communication such as a report sent through the mail. The results provided to a customer can inform the customer of the carrier status of the customer for one or more diseases or traits and/or the chances that the customer will develop one or more diseases or traits. After the customer has received results and referrals, the customer's order can be considered fulfilled, and results and referrals can remain accessible to the customer through an online website account. The customer can then choose to further pursue a referral offline if the customer so desires but outside of the purview of the website.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Schematic Description of the Novel Strategy for miRNA Quantification An exemplary schematic representation of a complementary sequence amplification scheme of the invention appears in FIG. 1. The RT loop primer contains three parts: the universal sequence (indicated by the line connecting Sequence A and Sequence B), the miRNA complementary sequence at the 5' end of the RT loop primer (Sequence A), and the miRNA complementary sequence at the 3' end of the RT loop primer (Sequence B). The RT reaction is initiated from the 3' end of the RT loop primer (Sequence B) and generates a hybrid cDNA strand that contains both miRNA and universal sequence. This RT with the specific loop primer uses reverse transcriptase in case of RNA target or primer extension with polymerase in case of DNA target. The polymerase knocks off the Sequence A hybridization to the target polynucleotide in its production of a complementary sequence to the region in a target polynucleotide 5' of the Sequence B hybridization region. After RT, the hybrid cDNA is quantified by qPCR using a forward primer which is complementary to the universal sequence and a reverse primer which is complementary to the miRNA-specific sequence.

Example 2: Target miRNAs and Primers

The sequences of mRNAs hsa-let-7a-5p (UGAGGU-AGUAGGUUGUAUAGUU, SEQ I.D NO:1, accession number MIMAT0000062, 22 nt) and hsa-let-7c (UGAGGU-AGUAGGUUGUAUGGUU, SEQ ID NO:2, accession number MIMAT0000064, 22 nt) were obtained from the miRBASE site: mirbase.org/index.shtml. The sequence of hsa-let-7x-test was generated by replacing a guanine of hsa-let-7a-5p to cytosine (UGAGGUAGUA CGUUGUAUAGUU, SEQ ID NO:3, 22 nt). The three synthetic miRNAs was simplified as let-7a, let-7c, and let-7x in this report. The synthetic miRNA oligonucleotides and primers were purchased from integrated DNA Technologies (IDT). The primers are named and have sequences listed 5 to 3' as the following:

"3 + 3":
(SEQ ID NO: 4)
ACCCTGTTGCAGTGGCCAATCGAGGAGGTCGAGAGGCTGAGAGATA;

"4 + 4":
(SEQ ID NO: 5)
ACCTCTGTTGCAGTGGCCAATCGAGGAGGTCGAGAGGCTGAGAGTATA;

"5 + 5":
(SEQ ID NO: 6)
ACCTACTGTTGCAGTGGCCAATCGAGGAGGTCGAGAGGCTGAGAGC-TATA;

"2 + 3":
(SEQ ID NO: 7)
ACCTGTTGCAGTGGCCAATCGAGGAGGTCGAGAGGCTGAGAGTAT;

"2 + 4":
(SEQ ID NO: 8)
ACCTGTTGCAGTGGCCAATCGAGGAGGTCGAGAGGCTGAGAGTATA;

"3 + 4":
(SEQ ID NO: 9)
ACCCTGTTGCAGTGGCCAATCGAGGAGGTCGAGAGGCTGAGAGTATA.

Example 3: Reverse Transcription and qPCR

The RT reaction solution contained 0.25 µg synthetic miRNA oligonucleotides and 0.7 µM RT primer. The RT buffer, dNTP, $MgCl_2$, RNaseOUT, and SuperScript® III RT were supplied by the kit SuperScript® III First-Strand Synthesis System (Invitrogen by life technology, 18080-051). RT was performed according to the manufacturer's instruction. Briefly, 10 µl reaction solutions were incubated in Bio-Rad CFX instrument at 37° C., 42° C. or 50° C. for 50 min, followed by 75° C. for 15 min, and then the RT yields were hold at 4° C.

The RT yields were analyzed by capillary electrophoresis (CE) instrument, the Fragment Analyzer (Advanced Analytical Technologies) along with the Sensitivity RNA Analysis Kit (DNF-489-0500) according to the manufacturer's instructions. The reaction contained RT primer but no miRNA template was set as RT control.

The qPCR was performed using TATAA SIB® Grandmaster® Mix according to the manufacturer's instruction. The cDNA generated from RT was diluted to approximate of $10^6$ copies/µl by TE-LPA buffer (8 µl of LPA was suspended in 10 ml 1x Tris-EDTA). Then 1 µl diluted cDNA and 200 nM PCR primers 5±5 Fp (universal, CTACTGTTGCAGTGG, SEQ ID NO:10, 22 nt) and 5+5 Rp (miRNA-specific, TGAGGTAGTAGGTTG, SEQ ID 22 nt) were added to the PCR reaction solution. The copy numbers of target cDNA in the reaction solution were calculated by the following formula: Copies of cDNA=Cone, of miRNA template (nM)×6.022 x/0 23 f (length of miRNA x 650×10<9>) The 10 µl reaction solution was incubated at 95° C. for 1 min, followed by 45 cycles of 95° C. for 5 s, 52° C. for 30 s, and 72° C. for 10 s. All reactions were run with duplications.

Example 4: Validation of the RT Process

To achieve the optimal specificity of miRNA quantification, we proposed a new strategy as exemplified in FIG. 1. Firstly, the hybrid cDNA template was obtained by reveres transcription with a primer containing 40 nt universal sequence and 5-10 nt miRNA-specific sequence. Then the qPCR was performed with a universal forward primer and a miRNA-specific reverse primer.

In this assay, both 5' and 3'-end of RT primers overlapped with the target miRNA. Therefore, one question was raised: how many nucleotides of RT primers are required to hybridize with target miRNA without interfering the performance of reverse transcriptase along with the miRNA template. To address this issue, different RT primers with various numbers of nucleotides complementary to 5' and 3'-end of the target miRNA were tested in Example 2.

Figure 2:
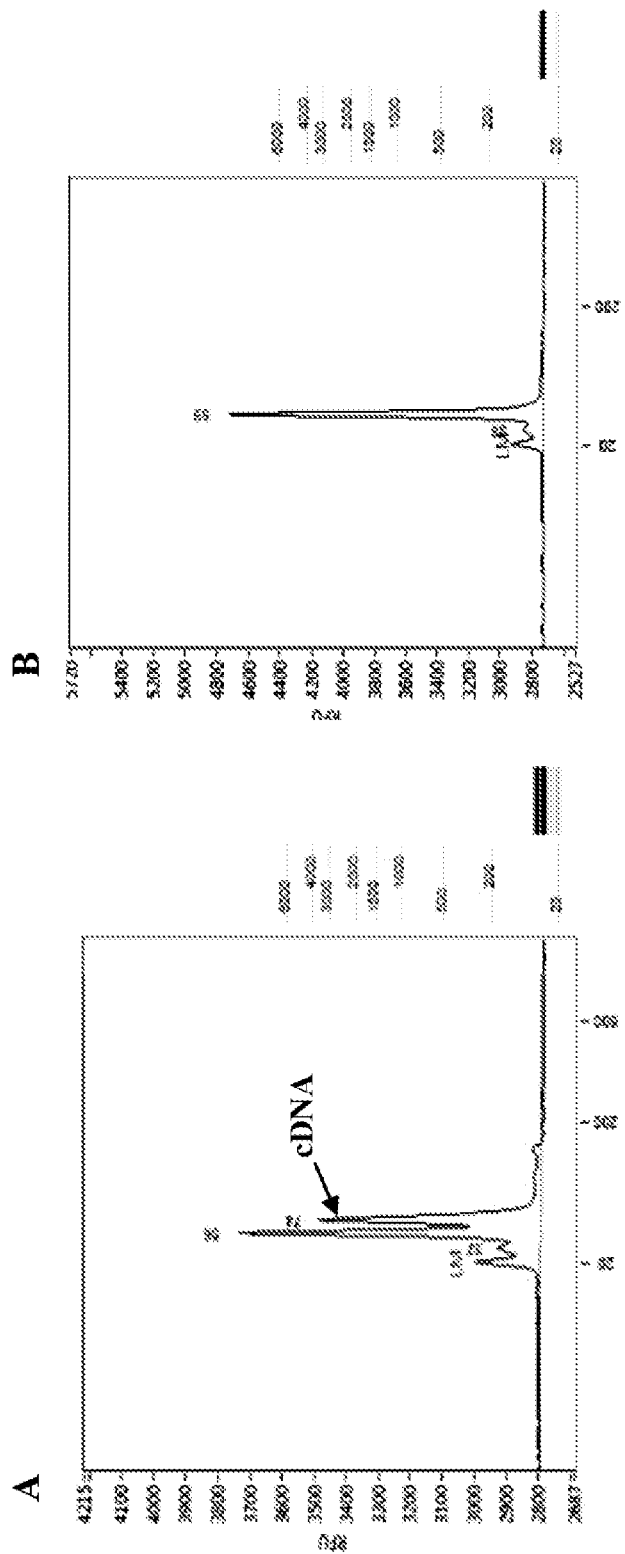
FIGS. 2A and 2B show an exemplary capillary electrophoresis (CE) analysis of the reverse-transcription (RT) yield generated by a specific primer according to an embodiment of the present disclosure.

There is efficient RT by RT primer "5+%". The RT reaction ijas firstly carried out at 50° C. The synthetic miRNA let-7a was applied as a template and the RT yields were analyzed by Cl. After RT with primer "5 t 5", an additional peak with 18 nt more than the RT primer was detected in FIG. 2 (part A), as compared to the RT control that contained no miRNA template in FIG. 2 (part B). In FIG. 2 (part A), the peak of the hybrid cDNA with approximate 74 nt is indicated by an arrow. FIG. 2 (part B) illustrates results for an RT control that contained primer 5+5 but no miRNA. LM indicates the 20-nt ladder marker.

Figure 3:
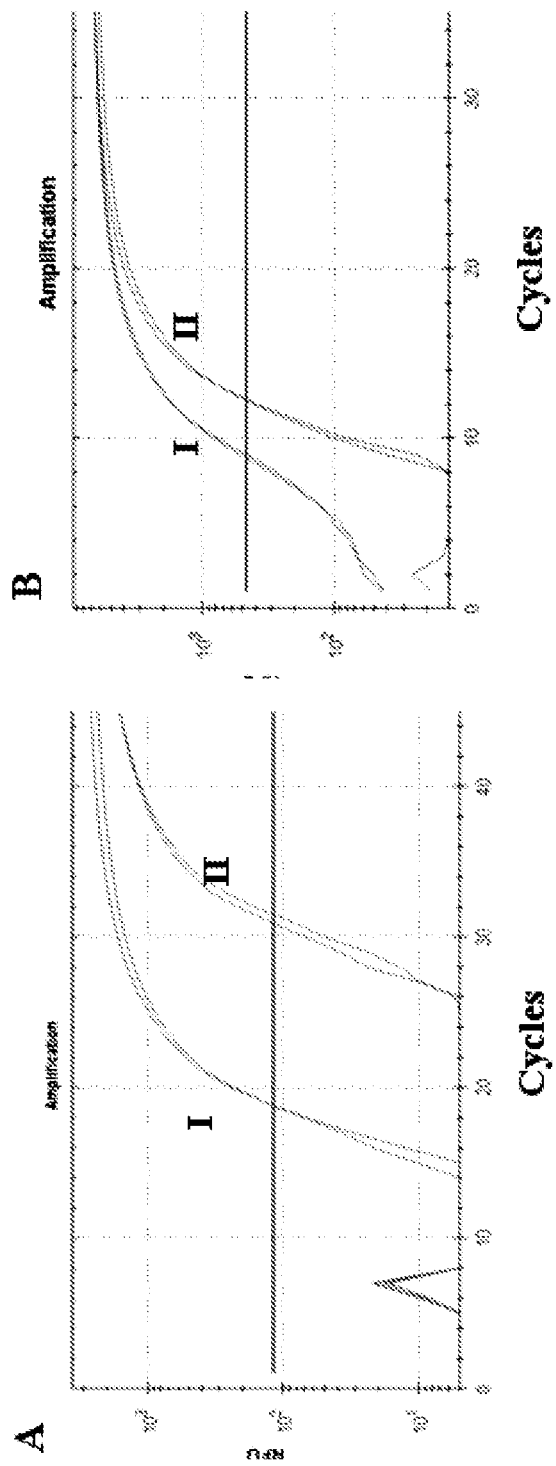
FIGS. 3A and 3B show an exemplary amplification of RT product by qPCR with different concentrations of primers according to an embodiment of the present disclosure.

The existence of the hybrid cDNA was further confirmed by qPCR with PCR primers 5+5 Fp and 5+5 Rp, as shown in FIG. 3 (part A). The concentration of RT primers was also important for the accuracy of miRNA quantification. We found that when the concentration of RT primer 5+5 was decreased from 1.4 to 0.7 µM, it showed little interference to the downstream qPCR without influencing the RT process in FIG. 3 (parts A and B). In FIG. 3 (part A), the RT product was generated by 0.7 µM RT primer 5+5. In FIG. 3 (part B), the RT product was generated by 1.4 M RT primer 5+5. For both FIG. 3 parts A and B, the amplification curve I was the amplicon of hybrid cDNA and the amplification curve II was the amplicon of RT control.

Figure 4:
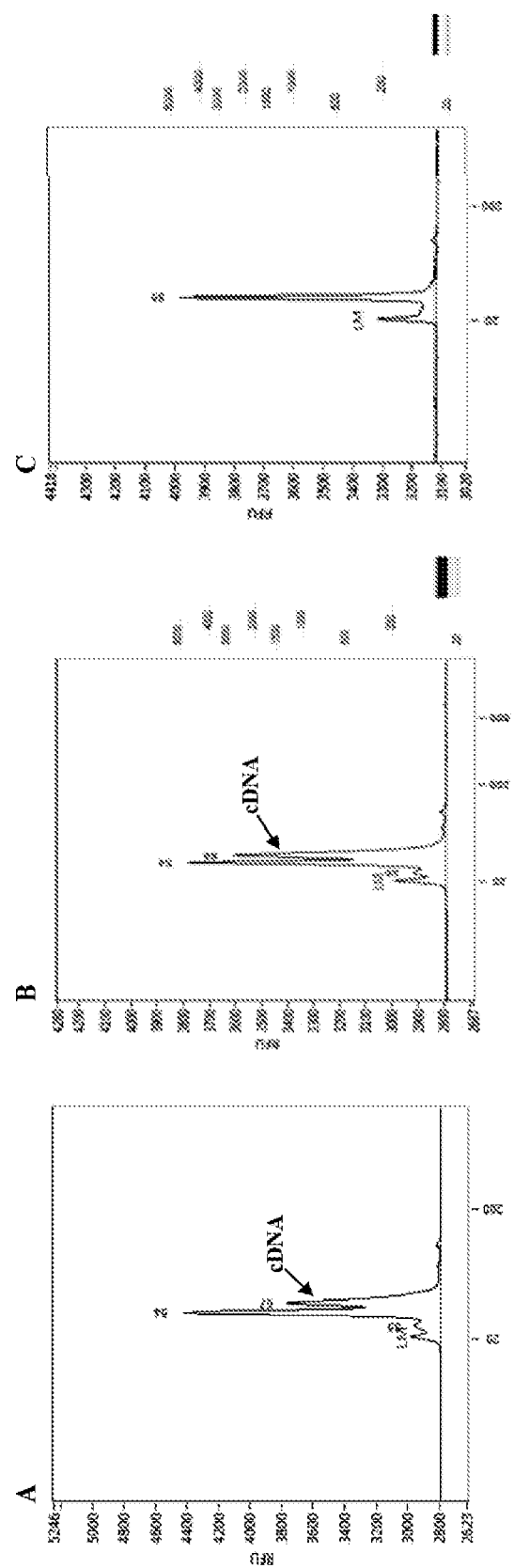
FIGS. 4A, 4B, and 4C show an exemplary CE analysis of RT yields generated by a specific primer at either 42° C. or 37° C. according to an embodiment of the present disclosure.

After performing the RT with other primers listed in Example 2, none of them generated the hybrid cDNA at 50° C. Considering the temperature may influence the result of RT, RT was carried out at 37° C. and 42° C., another two common RT temperatures used in laboratories. As shown in FIG. 4, the cDNA was generated by primer 5+5 at both temperatures. In contrast, still no hybrid cDNA was generated by other primer pairs at either of these 2 temperatures tested. In FIG. 4 (part A), RT was performed at 42° C. In FIG. 4 (part B), RT was performed at 37° C. In FIG. 4 (part C), RT control contained primer 5+5 but no miRNA. In FIG. 4, the newly generated cDNAs were indicated by an arrow; LM indicates the ladder maker; and RNA is indicated with 20 nt.

Figure 5:
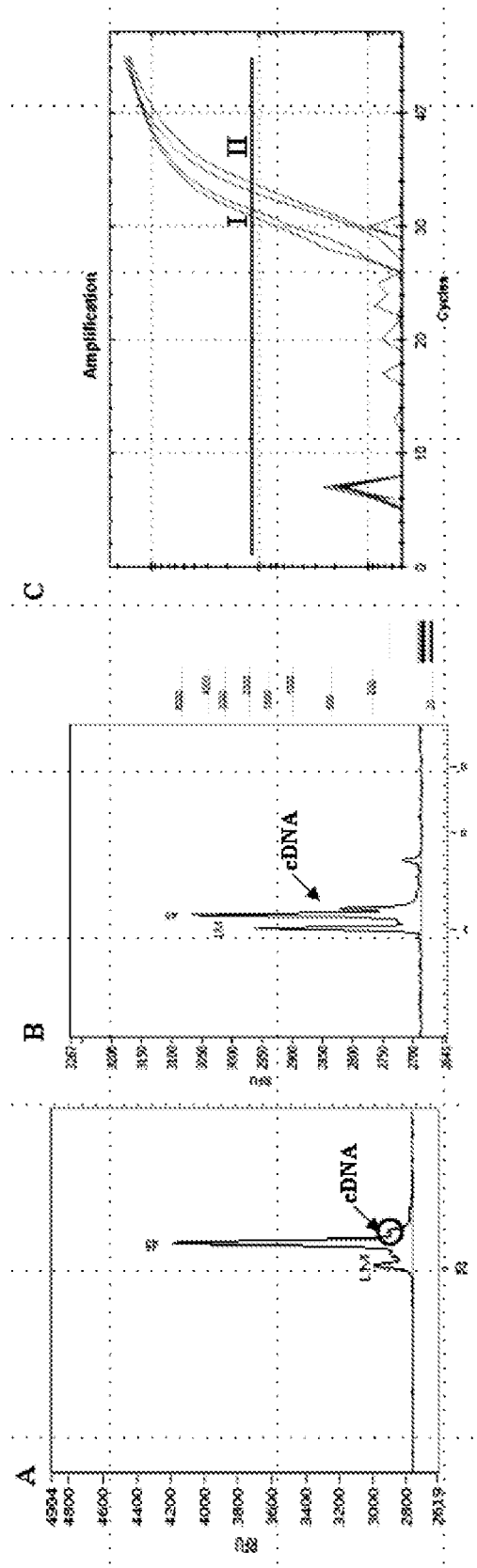

High concentration of RT primers may lead to false-negative reading of CE by compressing the signal of cDNA yield to low RFU. Therefore, the concentration of RT primers was lowered from 0.7 M to 0.28 M. Then an additional peak that might represent the hybrid cDNA yield was observed after RT with RT primer 3+3 in FIG. 5 (parts A and B). To assure the existence of hybrid cDNA, the RT products were validated by qPCR using primers 5+5 Fp and 5+5 Rp, and the Cq value was only 2.3 cycles more than that of RT control, as seen in FIG. 5 (part C). In FIG. 5 (part A), an additional peak in CE analysis representing the hybrid cDNA yield was observed when the concentration of RT primer 3+3 was 1.4 µM. In FIG. 5 (part B), an additional peak in CE analysis representing the hybrid cDNA yield was observed when the concentration of RT primer 3+3 was 2.8 µM. In FIG. 5 (part C), qPCR analysis shows that amplification curve I represented the amplicon of RT product generated by 0.28 M primer 3+3 and amplification curve II represented the amplicon of RT control (RT without miRNA template) that contained 0.28 M RT primer 3+3. In conclusion, the hybrid cDNA containing the target miRNA sequence can be reverse transcribed by primer pair 5+5. These results indicate that for this target under the conditions tested, 5 nt overlapping the miRNA sequence at 3'-end of RT primer was optimal for initiating RT process.

Example 5: Validation of Specificity

Figure 6:
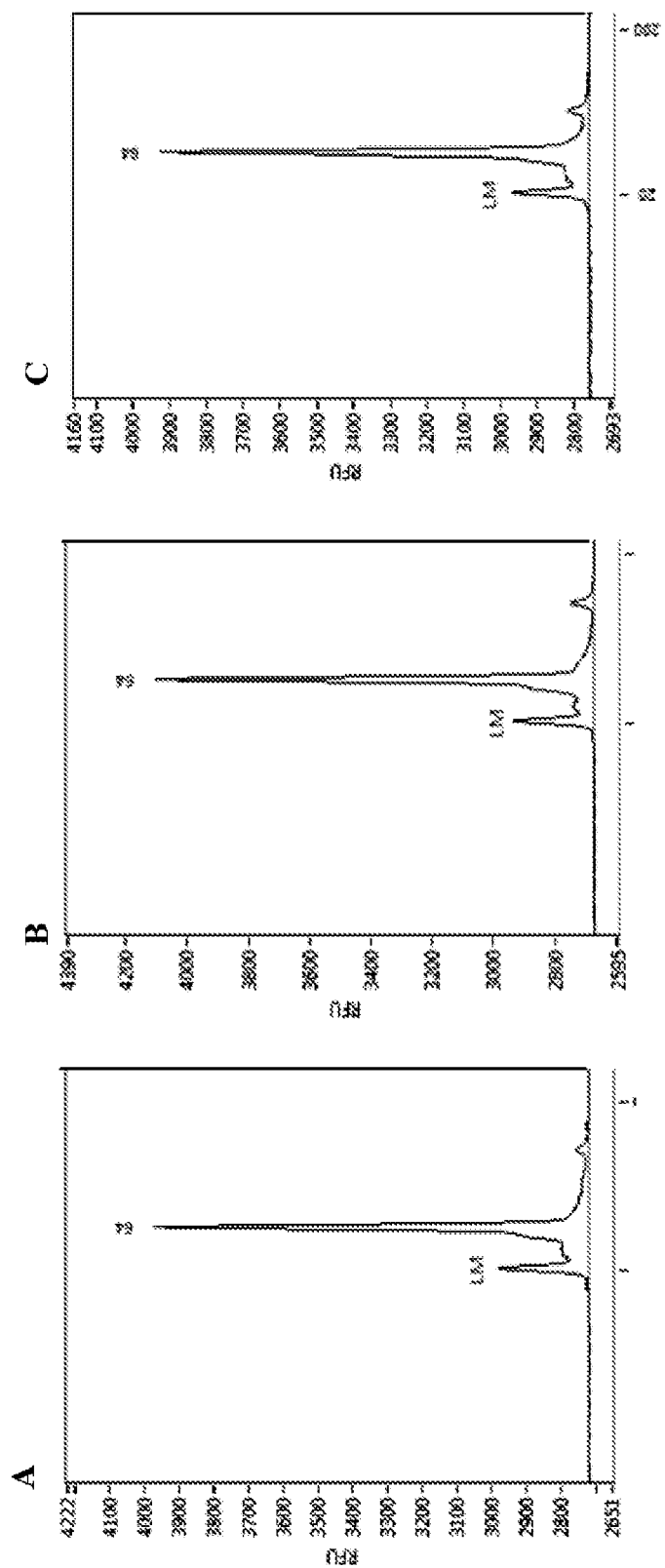
FIGS. 6A, 6B, and 6C show an exemplary CE analysis of RT products generate by different miRNAs with a specific RT primer according to an embodiment of the present disclosure.
Figure 8:
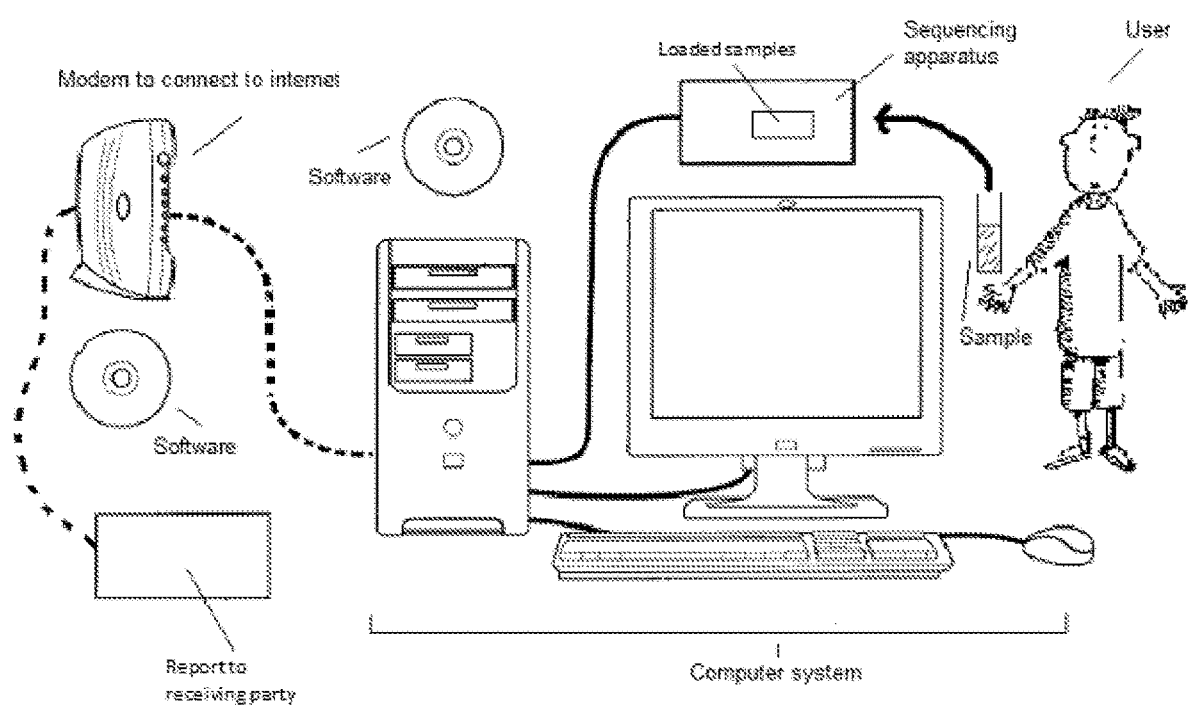
FIG. 8 illustrates a non-limiting example of a computer system useful in methods, compositions, reaction mixtures, kits, and/or systems of the disclosure.

The specificity of this assay was evaluated by using synthetic miRNAs of let-7c and let-7x that differ as few as only one nucleotide with let-7a. First, the specificity of RT is evaluated. The RT was performed with RT primer 5+5 that perfectly matched with let a. The yield of RT was examined by CE. The results indicated that similar amount of RT products were: generated from different miRNA templates, as shown in FIGS. 6A, 6B, and 6C. In FIG. 6 (part A), let-7a vas used as the RT template. In FIG. 6 (part B), let-7c was used as the RT template. In FIG. 6 (part C), let-7 was used as the RT template. LM indicates the 20 nt RNA ladder marker.

Second, the specificity of the qPCR was evaluated. The RT products were amplified by PCR primers 5+5 Fp and 5+5 Rp. The relative detection efficiency from Cq difference between perfectly match and mismatch targets were be calculated by the formula $2^{-(Cq\ unspecific-Cq\ specific)}$, assuming 100% efficiency for the perfect match. As shown in FIG. 7, as low as 1.48% of non-specific signal level was observed when comparing the amplification results of let-7a with let-7x. However, the specificity to discriminate let-7c from let-7a was low, showing 21.8% the relative detection efficiency of let-7c to let-7a. The experiment was repeated by using another batch of RT products and similar result was obtained. In FIG. 7, assuming the amplification efficiency of let-7a was 100%, the amplification Cq values of let-7c and let-7x were against to let-7a and the relative detection efficiency was calculated.

Though both let-7c and let-7x had one nucleotide mismatching with let-7a, the relative detection efficiency of let-7c and let-7x against let-7a were quite different. This difference might be determined by the position of mismatched nucleotide. As for let-7x, the mismatched nucleotide was located at 3'-end of the miRNA and can be covered by miRNA-specific PCR primer 5+5 Rp during the qPCR process. Therefore, the discrimination of let-7a from let-7x was achieved during both the process of RT and qPCR. Unlike the let-7x, the mismatched nucleotide of let-7c was hung at 5'-end of let-7c and there was no amplification selection during the qPCR process as let-7x did. Moreover the relative high non-specific signal might be due to the cross reaction of G-T during the RT process. From this point of view, the specificity of this miRNA quantification strategy might be significantly enhanced after the optimization of RT and qPCR primers.

Figure 9:
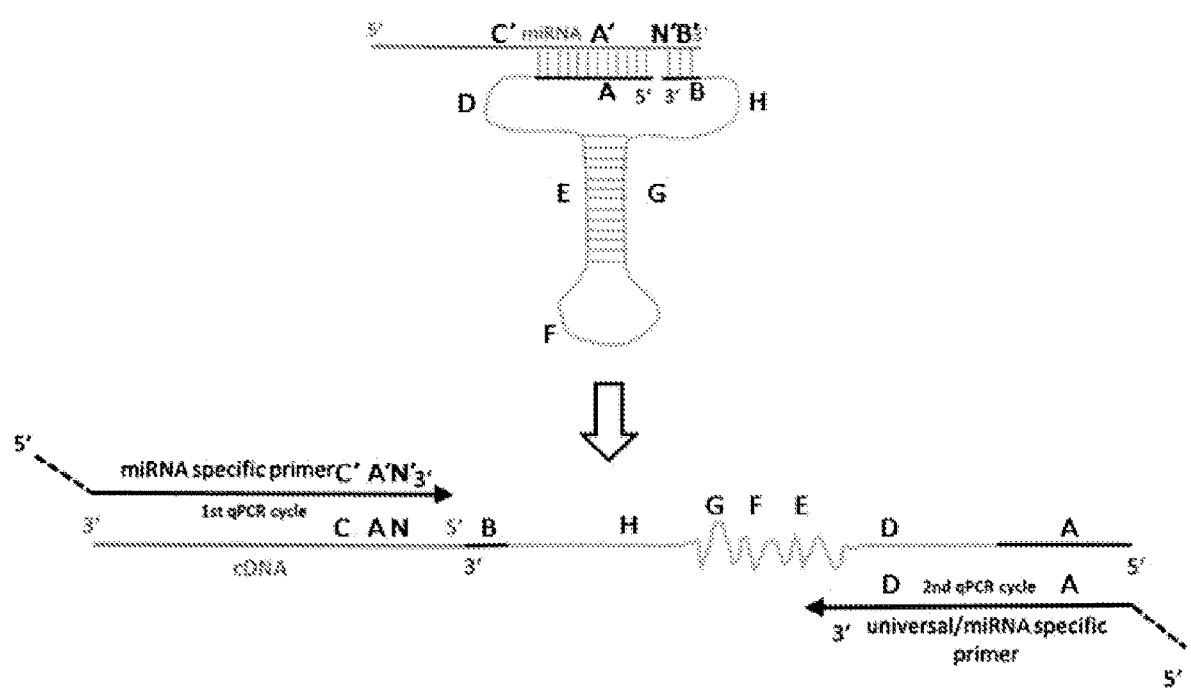
FIG. 9 depicts an exemplary schematic representation of a complementary sequence amplification scheme of the disclosure.

Example 6: Schematic Description of an Alternative Strategy for miRNA Quantification An exemplary schematic representation of an alternative structure of the loop primer, where part of the loop is folded into a hairpin structure, is shown in FIG. 9. The primer contains a 5' recognizing element (Sequence A), a 5'-arm sequence (Sequence D), a hairpin with a stem (Sequences E & G) and a loop (Sequence F), a 3'-arm sequence (Sequence H) and a 3' recognizing element (Sequence B). The hairpin stabilizes the loop structure and sequesters most of the bases from interacting with other nucleic acids in the sample, thus reducing background. The stem design can be adjusted to modify the characteristics of the system. An example of background reduction by introducing a hairpin structure into the loop primer is shown in FIG. 12.

Example 7: Validation of Specificity Using a Loop Primer Comprising a Hairpin

FIGS. 10A, 10B, and 10C show results for an analysis of the cross reactivity of seven assays based on the indicated loop primers targeting the first five members of the let 7 family (let7a-e) measured by RT and qPCR. The sequences of the hsa-let-7a-5p to hsa-let-7e-5p were obtained from the miRBASE (at the website available at mirbase.org). The RT and qPCR primers used are shown in FIG. 10 (part A), Two loop primers were designed against each of let7b and let7c.

The RT reactions were performed using TATAA GrandScript® Flex cDNA Synthesis Kit in 10 µl reaction volumes containing 12 pg synthetic miRNA oligonucleotides and 50 nM RT primers according to manufacturer's instruction. For each miRNA target, an RT-control was performed adding nuclease free water instead of reverse transcriptase. The reaction solutions were incubated in a Bio-Rad CFX96 instrument at 31° C. for 45 min, followed by 85° C. for 5 min, and then kept on hold at 4° C.

The qPCRs were performed using TATAA SYBR® GrandMaster® Mix in 10 µl reaction volumes containing 400 nM primers according to the manufacturer's instructions. The cDNA from the RT was diluted 5 times in nuclease free water and 2 µl was added to each qPCR, except for the NTCs where nuclease free water was added instead of cDNA. The reaction solutions were incubated in a Bio-Rad CFX384 instrument at 95° C. for 30 seconds, followed by 45 cycles of 95° C. for 5 seconds, 60° C. for 15 seconds, and 72° C. for 10 seconds, and then a melt curve from 65° C. to 95° C. in 0.5° C./second steps. All reactions were run in duplicates.

The Cq values obtained from the qPCRs are shown in FIG. 10 (part B) and the relative detection efficiencies, calculated by the formula $2^{-(C_q\ unspecific-C_q\ specific)}$, are shown in FIG. 10 (part C). The Cq values for the perfectly matched targets vary substantially, which may be due to variations in the template concentrations and/or variation in efficiency of loop primers in priming the reverse transcription of the RNA into cDNA. The cross re-activities were, with a few exceptions, below 2%, even though several of the targeted sequences differ only in a single base position. One of the loop primers designed to target let7c showed 20.1% cross reactivity to Let7b, but with the other let7c loop primer cross reactivity was reduced to 1.3%. Lower specificity was also observed for one of the loop primers designed to target Let7b with 12.4% cross reaction to Let7c. However, the other loop primer to Let7b showed a cross reactivity of only 1.6%.

Figure 11:
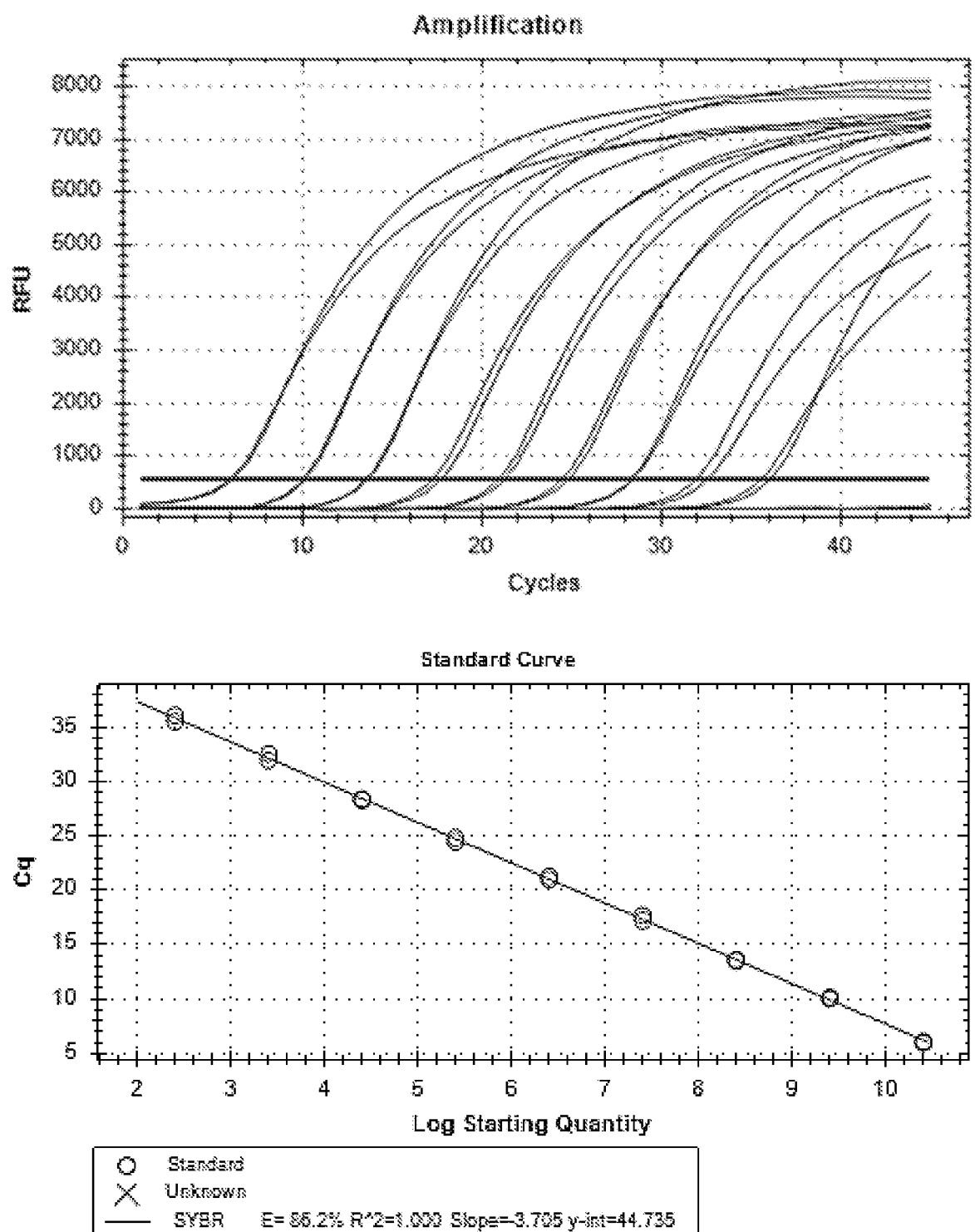
FIG. 11 provides results showing the target amplification sensitivity for miRNA family members (let-7 a, b, c, d and e) according to an embodiment of the present disclosure. Results indicate a sensitivity of at least about 25-250 copies of miRNA copies per μL. Assay efficiency was about 80-90%.
Figure 16A:
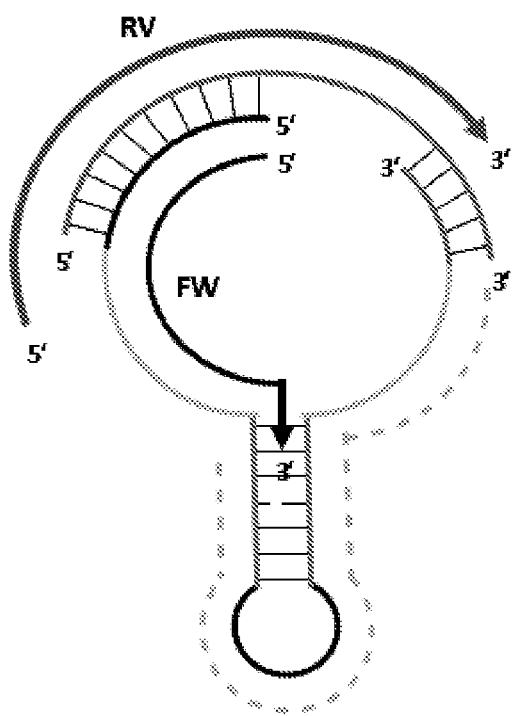

Example 8: Validation of Assay Efficiency Using Hairpin Loop Primers of the Invention The extensive range of the assays using hairpin loop primers is illustrated in FIG. 11. The input amount of miRNA hsp-let-7a-5p was varied from 2.5*10$^{10}$-250 copies/RT reaction. The assays show excellent linearity within the studied range and the efficiency of the qPCR system was about 86%.

The RT reactions ere performed using TATAA GrandScripts® flex cDNA Synthesis Kit in 10 µl reaction volumes containing 50 nM RT primer TACTACCTCAACTCCCTCGCGTTCGTTCTTCGACCGCACTCCGTCAACTA (SEQ ID NO: 12) according to manufacturer's instruction. An RT negative control was included using nuclease free water instead of reverse transcriptase to measure background signal. The reaction solutions were inncubated, in a Bio-Rad CFX96 instrument at 25° C. for 45 min, followed by 85° C. for 5 min, and then kept on hold at 4° C.

The qPCRs were performed using TATAA SYBR® GrandMaster® Mix in 10 µl reaction volumes containing 400 nM forward primer CCTCAACTCCCTCGCGTT (SEQ ID NO:13, and reverse primer GCCCATGAGGTAGTAGGTTGTATA (SEQ ID NO:14) according to the manufacturer's instructions. The cDNA from the RT was diluted 4 times is nuclease free water and 2 µl was added to each qPcR, except for the non template controls where nuclease free water was added instead of cDNA. The reaction solutions were incubated in a Bio Rad CFX384 instrument at 95° C. for 30 seconds, followed by 45 cycles of 95° C. for 5 seconds, 60° C. for 15 seconds, and 72° C. for 10 seconds, and then a melt curve from 65° C. to 95° C. in 0.5° C./second steps. All reactions were run in duplicates.

Example 9: Validation of Background Reduction Using a Loop Primer Comprising a Hairpin The design of the hairpin in the loop primer was altered to test the effect on the background signal. Four loop primers were designed with the same 3' and 5' recognizing elements, but with small variations in the hairpin, arm and loop sequences (FIG. 12). The Cq values for the positive reactions are very similar, ranging from 16.07 (RT18) to 16.44 (RT19), evidencing negligible effect of the modifications on the efficiency. The negative controls on the other hand show significantly higher variation, ranging from a Cq of 34.86 for the RT10 primer to a Cq>45 (no crossing observed when running 45 cycles) for RT18. This shows that background signal of an assay can be eliminated by fine tuning the design, without compromising the positive signal.

The RT reactions were performed using TATAA GrandScript® Flex cDNA Synthesis Kit in 10 µl reaction volumes containing 12 pg synthetic miRNA oligonucleotides and 50 nM RT primers according to manufacturer's instruction. For each target an RT-control was performed adding nuclease free water instead of reverse transcriptase. The reaction solutions were incubated in a Bio-Rad CFX96 instrument at 31° C. for 45 min, followed by 85° C. for 5 min, and then kept on hold at 4° C.

The qPCRs were performed using TAT: A SYBR® GrandMaster® Mix in 10 µl reaction volumes containing 400 nM forward primer TCACCCACCACGTACCGG (SEQ ID NO:15) and reverse primer GCGGCYGAGGYAGYAG-GYYGYA (SEC) ID NO:16) according to the manufacturer's instructions. The cDNA from the RT was diluted 4 times in nuclease free water and 2 µl was added to each qPCR, except for the non-template controls where nuclease tree water was added instead of cDNA. The reaction solutions were incubated in a Bio-Rad CFX384 instrument at 95'C for 30 seconds, followed by 45 cycles of 95° C. for 5 seconds, 60° C. for 15 seconds, and 72° C. for 10 seconds, and then a melt curve from 65° C. to 95° C. in 0.5° C./second steps. All reactions were run in duplicates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for producing a complementary sequence to a region in a target polynucleotide in a sample, the method comprising: subjecting the sample to a nucleic acid amplification reaction in a reaction mixture under conditions to yield the complete sequence complementary to the region of the target polynucleotide wherein the reaction mixture comprises:

(a) a loop primer that comprises sequence A, a linker sequence D, and sequence B, oriented from 5' to 3' on a single strand; wherein the loop primer specifically hybridizes to the target polynucleotide via (i) sequence complementarity between sequence A of the loop primer and sequence A' on the target polynucleotide, and (ii) sequence complementarity between sequence B of the loop primer and sequence B' on the target polynucleotide, wherein sequence A' and sequence B' are oriented 5' to 3' on the target polynucleotide; and (b) a polymerase that extends sequence B of the loop primer from 5' to 3' along the target polynucleotide that serves as the template for template-directed primer extension to produce the complementary sequence of the target polynucleotide, wherein the linker sequence D comprises a hairpin structure comprising a stem length of at least 5 base pairs, thereby producing a product of the nucleic amplification comprising the complete sequence complementary to the region of the target polynucleotide.

2. The method of claim 1, further comprising amplifying the product of claim 1 in the presence of a reverse primer and a forward primer, wherein the reverse primer specifically hybridizes to a sequence that is complementary to a portion of the target polynucleotide that is 5' with respect to sequence A' or B' and the forward primer specifically hybridizes to a sequence in the linker sequence D.

3. The method of claim 1, further comprising, detecting the product of claim 1 comprising detecting a signal from a detection probe in the reaction mixture that has a sequence complementary to the product or the complement thereof.

4. The method of claim 1, wherein sequence A is 2 to 10 nucleotides in length and sequence B is 2 to 10 nucleotides in length.

5. The method of claim 1, wherein the 3' end of sequence A' is within 5 nucleotides of sequence B'.

6. The method of claim 1, wherein the target polynucleotide is a non-coding RNA.

7. The method of claim 6, wherein the non-coding RNA is a microRNA (miRNA) molecule.

8. The method of claim 1, Wherein the linker sequence D comprises one or more sequence elements selected from the group consisting of a barcode sequence, a restriction enzyme recognition sequences, an oligonucleotide probe binding sequence or complement thereof, a sequencing primer annealing sequence, and a combination thereof.

9. A composition for producing a complementary sequence to a region in a target polynucleotide in a sample, the composition comprising a loop primer, a forward primer, and a reverse primer, wherein:

(a) the loop primer comprises sequence A, a linker sequence D, and sequence B, oriented from 5' to 3' on a single strand, wherein the loop primer specifically hybridizes to the target polynucleotide via (i) sequence complementarity between sequence A and sequence A' on the target polynucleotide, and (ii) sequence complementarity between sequence B and sequence B' on the target polynucleotide, wherein sequence A' and sequence B' are oriented 5' to 3' on the target polynucleotide;

(b) the reverse primer exhibits sequence homology to a sequence in the target polynucleotide located 5' with respect to sequence A'; and (c) the forward primer specifically hybridizes to a sequence in the linker sequence D, wherein the linker sequence D comprises a hairpin structure comprising a stem length of at least 5 base pairs.

10. The composition of claim 9, further comprising detection probe that has sequence complementarity to the target polynucleotide or complement thereof produced by extension of the reverse primer or the forward primer.

11. The composition of claim 9, further comprising the target polynucleotide, wherein the target polynucleotide is a non-coding RNA.

12. The composition of claim 10, wherein the non-coding RNA is a micro RNA (miRNA) molecule.

13. The composition of claim 9, wherein the linker sequence comprises a universal sequence common to multiple different loop primers.

14. A reaction mixture for producing a complementary sequence to a region in a target polynucleotide in a sample, the reaction mixture comprising a loop primer, a forward primer, a reverse primer, and a polymerase, wherein:

(a) the loop primer comprises sequence A, a linker sequence D, and sequence B, oriented from 5' to 3' on a single strand; wherein the loop primer specifically hybridizes to the target polynucleotide via (i) sequence complementarity between sequence A and sequence A' on the target polynucleotide, and (ii) sequence complementarity between sequence B and sequence B' on the target polynucleotide, wherein sequence A' and sequence B' are oriented 5' to 3' on the target polynucleotide;

(b) the reverse primer exhibits sequence homology to a sequence in the target polynucleotide located 5' with respect to sequence A'; and (c) the forward primer specifically hybridizes to a sequence in the linker sequence, wherein the linker sequence D comprises a hairpin structure comprising a stem length of at least 5 base pairs.

15. The reaction mixture of claim 14, further comprising a detection probe that has sequence complementarily to the target polynucleotide or complement thereof produced by extension of the reverse primer or the forward primer.

16. The composition of claim 9, wherein the region in the target polynucleotide (C') is oriented 5' of sequence A' and sequence B' on the target polynucleotide.

17. The composition of claim 16, wherein the complementary sequence of the region in the target polynucleotide that is produced is sequence C, and the complementary sequence of the target polynucleotide that is produced is oriented 5' to 3' A-D-B-A-C.

18. The composition of claim 9, wherein the hairpin structure in the linker sequence D is at least 10 nucleotides in length.

19. The reaction mixture of claim 14, wherein the region in the target polynucleotide (C') is oriented 5' of sequence A' and sequence B' on the target polynucleotide.

20. The reaction mixture of claim 19, wherein the complementary sequence of the region in the target polynucleotide that is produced is sequence C, and the complementary sequence of the target polynucleotide that is produced is oriented 5' to 3' A-D-B-A-C.

21. The reaction mixture of claim 14, wherein the hairpin structure in the linker sequence D is at least 10 nucleotides in length.

* * * * *

SEQUENCE LISTING

<160> NUMBER OF SEQ ID NOS: 48

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugagguagua gguuguauag uu                                                  22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugagguagua gguuguaugg uu                                                  22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ugagguagua cguuguauag uu                                                  22

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accctgttgc agtggccaat cgaggaggtc gagaggctga gagata                        46

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acctctgttg cagtggccaa tcgaggaggt cgagaggctg agagtata                      48

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acctactgtt gcagtggcca atcgaggagg tcgagaggct gagagctata                    50

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acctgttgca gtggccaatc gaggaggtcg agaggctgag agtat            45

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acctgttgca gtggccaatc gaggaggtcg agaggctgag agtata           46

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accctgttgc agtggccaat cgaggaggtc gagaggctga gagtata          47

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctactgttgc agtgg                                             15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaggtagta ggttg                                             15

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tactacctca actccctcgc gttcgttgtt cgaccgcact ccgtcaacta       50

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctcaactcc ctcgcgtt                                                 18

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcccatgagg tagtaggttg tata                                          24

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcacccacca cgtacgg                                                  17

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcggctgagg tagtaggttg ta                                            22

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tactacctca cccaccacgt acggctagaa gacgtaccat ctgcaaacta              50

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tactacctca cccaccacg                                                19

```
<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcggctgagg tagtaggttg tata                                              24

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugagguagua gguugugugg uu                                                22

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tactacctca cccaccacgt acggctagaa gacgtaccat ctgcaaacca c                51

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggctgaggt agtaggttgt g                                                 21

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tactacctca cccaccacgt acggctagaa gacgtaccat ctgcaaacc                   49

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tactacctca cccaccacgt acggctagaa gacgtaccat ctgcaaacca                  50

<210> SEQ ID NO 25
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tactacctca cccaccacgt acggctagaa gacgtaccat ctgcaaacca t            51

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cggctgaggt agtaggttgt atg                                           23

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
agagguagua gguugcauag u                                             21

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tactacctct cccaccacgt acggctagaa gacgtaccat ctgcaactat g            51

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tactacctct cccaccacg                                                19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cggcagaggt agtaggttgc                                               20

<210> SEQ ID NO 31
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugagguagga gguuguauag u                                             21

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcctacctca cccaccacgt acggctagaa gacgtaccat ctgcaactat a            51

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcctacctca cccaccac                                                 18

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcggctgagg taggagg                                                  17

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tactacctca actccttccc gttcgttgtt cgaccggact ccgttaacta              50

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tactacctca actccttctc ggttcgttgt tcgacccgac tccgttaact a            51

<210> SEQ ID NO 37
<211> LENGTH: 48
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 37
ctacctcacc caccacgtac ggctagaaga cgtaccatct gcaaacta          48

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cctcacccac acgtacggc tagaagacgt accatctgca aacta              45

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctcacccacc acgtacggct agaagacgta ccatctgcaa acta               44

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcacccacca cgtacggcta gaagacgtac catctgcaaa cta                43

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tactacctca cccaccacgt acggctagaa gacgtaccat ctgcaaacta t       51

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tactacctca cccaccacgt acggctagaa gacgtaccat ctgcaaacta ta      52

<210> SEQ ID NO 43
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 43
caacctgcca caccgac                                                        17

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tctgctcaac ta                                                             12

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
caacctgcga gactctacat                                                     20

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtactgctca aacta                                                          15

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caacctgcga gactctacat ga                                                  22

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtactgctca atgaaacta                                                      19
```